(12) United States Patent
Mowat et al.

(10) Patent No.: US 12,276,600 B2
(45) Date of Patent: Apr. 15, 2025

(54) SYSTEMS AND METHODS FOR DETECTING FOODBORNE PATHOGENS USING SPECTRAL ANALYSIS

(71) Applicant: Hyperspectral Corp., Alexandria, VA (US)

(72) Inventors: Euan Mowat, Alexandria, VA (US); Matthew Theurer, Alexandria, VA (US); Sarah Rachel Hernandez, Austin, TX (US); Mario Martinez, Alexandria, VA (US)

(73) Assignee: Hyperspectral Corp., Alexandria, VA (US)

( * ) Notice: Subject to any disclaimer, the term of this patent is extended or adjusted under 35 U.S.C. 154(b) by 176 days.

(21) Appl. No.: 18/173,035

(22) Filed: Feb. 22, 2023

(65) Prior Publication Data

US 2023/0266236 A1    Aug. 24, 2023

Related U.S. Application Data

(60) Provisional application No. 63/268,352, filed on Feb. 22, 2022, provisional application No. 63/268,355, (Continued)

(51) Int. Cl.
*G01N 21/31* (2006.01)
*G01N 21/01* (2006.01)
*G01N 21/27* (2006.01)

(52) U.S. Cl.
CPC ......... *G01N 21/314* (2013.01); *G01N 21/274* (2013.01); *G01N 2021/0125* (2013.01); (Continued)

(58) Field of Classification Search
None
See application file for complete search history.

(56) References Cited

U.S. PATENT DOCUMENTS

2010/0285523 A1    11/2010    Pinsky et al.
2011/0307423 A1    12/2011    Shotton et al.
(Continued)

OTHER PUBLICATIONS

Davis et a l. "Fourier transform infrared (FT-IR) spectroscopy: a rapid tool for detection and analysis of foodborne pathogenic bacteria." Current research, technology and education topicsIn applied microbiology and microbial biotechnology 2 (2010): 1582-1594. Retrieved on May 29, 2023 {May 29, 2023) from entire document.

(Continued)

*Primary Examiner* — Violeta A Prieto
(74) *Attorney, Agent, or Firm* — Ahmann Kloke LLP

(57) ABSTRACT

An example system includes a light intensity measuring apparatus couplable to a food processing apparatus and a computing system. The light intensity measuring apparatus includes a chamber configured to receive a water sample from the food processing apparatus, a light source, a detector configured to detect light that has passed through the water sample and measure multiple times intensities of wavelengths of the light to obtain multiple sets of measured intensities of wavelengths, and a communication module configured to provide the multiple sets of measured intensities of wavelengths. The computing system may receive the multiple sets of measured intensities, process the multiple sets to obtain a set of values, apply a first set of decision trees to the set of values to obtain a first result indicating a positive or negative foodborne pathogen detection, generate a notification indicating either the positive of negative detection, and provide the notification.

20 Claims, 17 Drawing Sheets

Related U.S. Application Data filed on Feb. 22, 2022, provisional application No. 63/268,349, filed on Feb. 22, 2022.

(52) U.S. Cl.
CPC ............... *G01N 2021/317* (2013.01); *G01N 2201/0484* (2013.01); *G01N 2201/061* (2013.01); *G01N 2201/12784* (2013.01)

(56) References Cited

U.S. PATENT DOCUMENTS

| | | | |
|---|---|---|---|
| 2015/0247190 A1 | 9/2015 | Ismagilov et al. | |
| 2015/0293094 A1 | 10/2015 | Ladisch et al. | |
| 2017/0082613 A1 | 3/2017 | Siciliano et al. | |
| 2022/0220547 A1* | 7/2022 | Dominguez-Nunez | C12Q 1/689 |
| 2023/0268082 A1* | 8/2023 | Hernandez | G01N 21/31 |
| | | | 600/300 |
| 2024/0019378 A1* | 1/2024 | Theurer | G01N 33/02 |
| 2024/0027266 A1* | 1/2024 | Mowat | G01J 3/501 |
| 2024/0145040 A1* | 5/2024 | Mowat | G01N 21/51 |

OTHER PUBLICATIONS

International Application No. PCT/US2023/063084, International Search Report and the Written Opinion, dated Jul. 11, 2023, 18 pages.

\* cited by examiner

SYSTEMS AND METHODS FOR DETECTING FOODBORNE PATHOGENS USING SPECTRAL ANALYSIS

CROSS-REFERENCE TO RELATED APPLICATIONS

This application claims priority to U.S. Provisional Patent Application No. 63/268,349, filed on Feb. 22, 2022 and entitled "OPTICAL VORTEX ARRAY SPECTROMETER," to U.S. Provisional Patent Application No. 63/268,352, filed on Feb. 22, 2022 and entitled "SYSTEMS AND METHODS FOR USING SCALOGRAMS WITH HYPERSPECTRAL DATA TO SCREEN FOR PARTICLES OF INTEREST," and to U.S. Provisional Patent Application No. 63/268,355, filed on Feb. 22, 2022 and entitled "SYSTEM AND METHOD FOR USING A STRATIFIED MULTI-MODEL ML SYSTEM WITH HYPERSPECTRAL DATA," and is related to application U.S. patent application Ser. No. 18/173,050, filed on the same day and entitled "SYSTEMS AND METHODS FOR DETECTING PATHOGENS USING SPECTROMETER SCANS," each of which is incorporated in its entirety herein by reference.

FIELD OF THE INVENTION(S)

Embodiments of the present invention(s) are generally related to detecting foodborne pathogens using spectral analysis, and in particular to detecting foodborne pathogens using spectral analysis, of food processing byproducts.

BACKGROUND

Foodborne illnesses may be caused by consuming food or beverages that are contaminated by pathogens such as bacteria, toxins produced by bacteria, viruses, parasites, chemicals, foreign material (e.g., metal shavings) and/or the like. The United States Food and Drug Administration (U.S. FDA) estimates that there are approximately 48 million cases of foodborne illness each year in the United States. The U.S. FDA further estimates that 1 in 6 Americans are affected by foodborne illnesses, resulting in 128,000 hospitalizations and 3,000 deaths.

Food or beverages (collectively, food) may be contaminated during any stage in the supply chain (e.g., in the field, while undergoing processing at food production or processing facilities (collectively, food processing facilities), or during shipping or transport). However, the contamination may not be discovered until after people are sickened from consuming the food. Unfortunately, government agencies, such as the U.S. FDA, often declare an outbreak of a foodborne illness and issue recalls of the food suspected of causing the outbreak only after a number of people are sickened.

In addition to the deleterious effects on individual health, there are economic costs to recalls. For example, a food producer or processor (collectively, a food processor) may voluntarily or be required to recall numerous lots of food or entire production runs. Such recalls may sicken many and may tarnish the brand of the food processor, leading to consumer distrust reduced sales, and large costs for product recalls, legal defense, and damage control.

SUMMARY

An example system includes a light intensity measuring apparatus couplable to a food processing apparatus and a computing system. The light intensity measuring apparatus includes a chamber configured to receive a water sample from the food processing apparatus, a light source configured to generate light, a detector configured to detect the light that has passed through at least a portion of the water sample in the chamber and measure multiple times intensities of wavelengths of the light to obtain multiple sets of measured intensities of wavelengths, and a communication module configured to provide the multiple sets of measured intensities of wavelengths. The computing system includes at least one processor, and memory containing instructions. The instructions are executable by the at least one processor to receive the multiple sets of measured intensities of wavelengths, process the multiple sets of measured intensities of wavelengths to obtain a set of values, apply a first set of decision trees to the set of values to obtain a first result, the first result indicating either a first positive foodborne pathogen detection or a first negative foodborne pathogen detection for a first foodborne pathogen, generate a first foodborne pathogen detection notification indicating either the first positive foodborne pathogen detection or the first negative foodborne pathogen detection for the first foodborne pathogen, and provide the first foodborne pathogen detection notification.

In various embodiments, the instructions are further executable by the at least one processor to apply a second set of decision trees to the set of values to obtain a second result, the second result indicating either a second positive foodborne pathogen detection or a second negative foodborne pathogen detection for a second foodborne pathogen, the second foodborne pathogen different from the first foodborne pathogen, generate a second foodborne pathogen detection notification indicating either the second positive foodborne pathogen detection or the second negative foodborne pathogen detection for the second foodborne pathogen, and provide the second foodborne pathogen detection notification.

In various embodiments, the instructions executable by the at least one processor to process the multiple sets of measured intensities of wavelengths to obtain the set of values include instructions being executable by the at least one processor to for multiple wavelengths, calculate a particular profile intensity utilizing particular intensities of wavelengths included in the multiple sets of measured intensities of wavelengths to obtain multiple profile intensities, calculate slopes of the multiple profile intensities at multiple wavelengths to obtain a set of slopes, and apply a fitting function to the set of slopes to obtain the set of values.

In various embodiments, the instructions are further executable by the at least one processor to remove from each of the multiple sets of measured intensities of wavelengths a first set of intensities of wavelengths not associated with presences of one or more pathogens.

In various embodiments, the light intensity measuring apparatus further includes a supply valve coupled to a first opening of the chamber and couplable to a water sample supply line couplable to the food processing apparatus, a drain valve coupled to a second opening of the chamber, and a valve control module configured to control the supply valve to open to allow the water sample from the food processing apparatus to flow into the chamber via the first opening and to control the drain valve to open to allow the water sample to flow out of the chamber via the second opening.

In various embodiments, the system further includes a cleaning fluid container configured to contain cleaning fluid, and a cleaning fluid supply line couplable to the cleaning fluid container and the supply valve. The valve control module is further configured to control the supply valve to open to allow cleaning fluid from the cleaning fluid container to flow into the chamber via the first opening and to control the drain valve to open to allow the cleaning fluid to flow out of the chamber via the second opening.

In various embodiments, the light intensity measuring apparatus further includes a transducer coupled to the chamber, and a transducer control module configured to control the transducer to move the chamber.

An example method includes receiving in a chamber of a light intensity measuring apparatus a sample of a food processing byproduct, generating light to pass through at least a portion of the sample, detecting the light that has passed through the at least portion of the sample, measuring multiple times intensities of wavelengths of the light to obtain multiple sets of measured intensities of wavelengths, processing the multiple sets of measured intensities of wavelengths to obtain a set of values, applying a first set of decision trees to the set of values to obtain a first result, the first result indicating either a first positive foodborne pathogen detection or a first negative foodborne pathogen detection for a first foodborne pathogen, generating a first foodborne pathogen detection notification indicating either the first positive foodborne pathogen detection or the first negative foodborne pathogen detection for the first foodborne pathogen, and providing the first foodborne pathogen detection notification.

In various embodiments, the method further includes applying a second set of decision trees to the set of values to obtain a second result, the second result indicating either a second positive foodborne pathogen detection or a second negative foodborne pathogen detection for a second foodborne pathogen, generating a second foodborne pathogen detection notification indicating either the second positive foodborne pathogen detection or the second negative foodborne pathogen detection for a second foodborne pathogen, and providing the second foodborne pathogen detection notification.

In various embodiments, processing the multiple sets of measured intensities of wavelengths to obtain the set of values includes for multiple wavelengths, calculating a particular profile intensity utilizing particular intensities of wavelengths included in the multiple sets of measured intensities of wavelengths to obtain multiple profile intensities, calculating slopes of the multiple profile intensities at multiple wavelengths to obtain a set of slopes, and applying a fitting function to the set of slopes to obtain the set of values.

In various embodiments, calculating the particular profile intensity utilizing particular intensities of wavelengths included in the multiple sets of measured intensities of wavelengths to obtain multiple profile intensities includes calculating a particular average intensity utilizing the particular intensities of wavelengths included in the multiple sets of measured intensities of wavelengths to obtain multiple average intensities.

In various embodiments, applying the fitting function to the set of slopes to obtain the set of values includes applying a smoothing filter to the set of slopes to obtain the set of values.

In various embodiments, processing the multiple sets of measured intensities of wavelengths to obtain the set of values further includes removing from each of the multiple sets of measured intensities of wavelengths a first set of intensities of wavelengths not associated with presences of one or more pathogens.

In various embodiments, the light intensity measuring apparatus performs the receiving, the generating light, the detecting, and the measuring, and a foodborne pathogen detection system distinct from the light intensity measuring apparatus performs the processing, the applying, the generating the first foodborne pathogen detection notification and the providing.

An example non-transitory computer-readable medium includes executable instructions, the executable instructions being executable by one or more processors to perform a method. The method includes receiving in a chamber of a light intensity measuring apparatus a sample of a food processing byproduct, generating light to pass through at least a portion of the sample, detecting the light that has passed through the at least portion of the sample, measuring multiple times intensities of wavelengths of the light to obtain multiple sets of measured intensities of wavelengths, processing the multiple sets of measured intensities of wavelengths to obtain a set of values, applying a first set of decision trees to the set of values to obtain a first result, the first result indicating either a first positive foodborne pathogen detection or a first negative foodborne pathogen detection for a first foodborne pathogen, generating a first foodborne pathogen detection notification indicating either the first positive foodborne pathogen detection or the first negative foodborne pathogen detection for a first foodborne pathogen, and providing the first foodborne pathogen detection notification.

In various embodiments, the method further includes applying a second set of decision trees to the set of values to obtain a second result, the second result indicating either a second positive foodborne pathogen detection or a second negative foodborne pathogen detection for a second foodborne pathogen, generating a second foodborne pathogen detection notification indicating either the second positive foodborne pathogen detection or the second negative foodborne pathogen detection for a second foodborne pathogen, and providing the second foodborne pathogen detection notification.

In various embodiments, processing the multiple sets of measured intensities of wavelengths to obtain the set of values includes for multiple wavelengths, calculating a particular profile intensity utilizing particular intensities of wavelengths included in the multiple sets of measured intensities of wavelengths to obtain multiple profile intensities, calculating slopes of the multiple profile intensities at multiple wavelengths to obtain a set of slopes, and applying a fitting function to the set of slopes to obtain the set of values.

In various embodiments, calculating the particular profile intensity utilizing particular intensities of wavelengths included in the multiple sets of measured intensities of wavelengths to obtain multiple profile intensities includes calculating a particular average intensity utilizing the particular intensities of wavelengths included in the multiple sets of measured intensities of wavelengths to obtain multiple average intensities.

In various embodiments, applying the fitting function to the set of slopes to obtain the set of values includes applying a smoothing filter to the set of slopes to obtain the set of values.

In various embodiments, processing the multiple sets of measured intensities of wavelengths to obtain the set of values further includes removing from each of the multiple sets of measured intensities of wavelengths a first set of intensities of wavelengths not associated with presences of one or more pathogens.

BRIEF DESCRIPTION OF THE DRAWINGS

Throughout the drawings, like reference numerals will be understood to refer to like parts, components, and structures.

DETAILED DESCRIPTION

Figure 1:
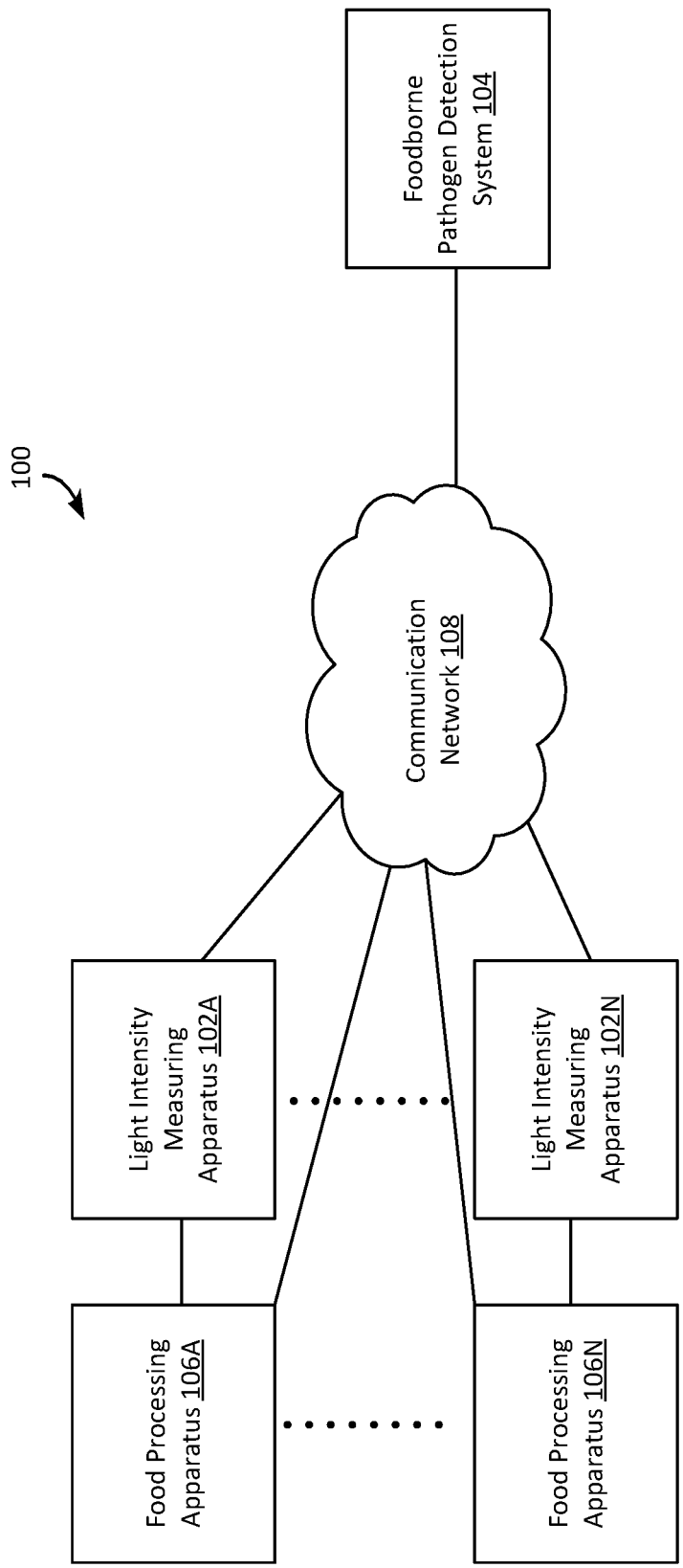
FIG. 1 depicts an example foodborne pathogen detection environment in some embodiments.

A government agency such as the U.S. FDA may not declare a foodborne illness outbreak until after a large number of persons have been sickened. Before declaring the outbreak, the government agency may have to perform an investigation to determine the food that is causing the outbreak, which may be difficult to do and/or take significant time. If the government agency is able to determine the food, testing for foodborne pathogens has to be performed to identify the particular foodborne pathogen responsible for the foodborne illnesses. The investigation and testing may take a large amount of time, during which more persons may be affected by the contaminated food. One reason for the large amount of time is that it may take approximately 48 hours to approximately 72 hours, to obtain test results confirming a foodborne pathogen.

In various embodiments, systems and methods discussed herein may enable early detection of foodborne pathogens during food production or processing (collectively, food processing) at food processing facilities. The systems may utilize light intensity measuring apparatuses, which may be or include spectrometers, to scan water used or produced by food processing apparatuses. The light intensity measuring apparatuses may transmit the spectrometer scans to a foodborne pathogen detection system that utilizes machine learning (ML) and/or artificial intelligence (AI) models to detect evidence of foodborne pathogens in the spectrometer scans. The foodborne pathogen detection system sends results to the light intensity measuring apparatuses to inform personnel working in the food processing facilities. In the event of a positive detection of a foodborne pathogen, the personnel may stop food processing and start remedial measures, such as cleaning food processing equipment, discarding contaminated food, and/or performing additional testing or detection.

Such early detection of foodborne pathogens allows food processors to identify contaminated food prior to shipping the food out to wholesalers, distributors, retailers, and/or consumers. This early detection may save food processors the costs of recalling food, which may be significant. In addition, early detection may prevent or reduce the occurrence of foodborne illness outbreaks, which may prevent or reduce illnesses, hospitalizations, and deaths.

In various embodiments, the systems and methods described herein are applicable to detect a wide variety of foodborne pathogens that cause foodborne illnesses. Such foodborne pathogens include norovirus, *salmonella* (non-typhoidal), *Clostridium perfringens, campylobacter, Staphylococcus aureus, Toxoplasma gondii, Escherichia coli* (*E. coli*), *Clostridium botulinum, cryptosporidium, Cyclospora*, hepatitis A virus, *shigella, Yersinia*, and *Listeria monocytogenes* (*listeria*), among many others. The foodborne pathogen detection systems may train one or more ML and/or AI models for each foodborne pathogen. Upon receiving spectral data from a light intensity measuring apparatuses, the foodborne pathogen detection systems may apply the trained machine learning and/or AI models to the spectral data. In this way, the foodborne pathogen detection systems may be able to detect multiple foodborne pathogens from spectral data of a single sample of a food processing byproduct. One advantage of some embodiments of the systems and methods described herein is that they may decrease the Limit of Detection (LOD) from the Classical Limit of Detection (cLOD), that is limited by physics, to the machine learning limit of detection (miLOD) that may be one to two orders of magnitude lower than the cLOD.

In various embodiments, the light intensity measuring apparatuses may be or include spectrometers or other spectral analysis technology, such as commercially available spectrometers or customized UV/VIS/NIR/MWIR/LWIR sensors that are capable of communicating with the foodborne pathogen detection system or are couplable to digital devices capable of communicating with the foodborne pathogen detection system. Food processors may widely deploy the light intensity measuring apparatuses at food processing facilities to detect foodborne pathogens in their food processing. The foodborne pathogen detection systems and associated methods described herein, because they provide more accurate results more quickly and economically than other systems and methods, are broadly applicable to any location where food is processed, such as farms, food processing facilities, packaging facilities, distributors, restaurants, grocery stores, homes, and other locations. Accordingly, the foodborne pathogen detection systems and associated methods described herein may provide significant benefits to farmers, food processors, distributors, restaurant operators, grocery store operators, households, consumers, and others (e.g., any entity in the farm to fork supply chain).

The foodborne pathogen detection systems and associated methods, due to the ability to perform rapid and continuous testing of foods, also allow for food processors to quarantine food that may be contaminated by foodborne pathogens prior to shipping out such food. For example, a food processor, upon detection of a foodborne pathogen during a particular food processing run, may be able to quarantine food processed during that run or food processed after the last "clean" test prior to shipping out that food. The food processor may then test the food (e.g., using laboratory tests) to confirm the presence of foodborne pathogens. The food processor may also be able to clean food processing equipment and/or parts of the food processing facility to prevent or reduce contamination of further food. The food processor may then retest food processing byproducts and/or equipment for contamination. As a result, the food processor may confirm that the machinery and/or byproducts are "clean" (e.g., without detected foodborne pathogens) before returning to food processing.

Accordingly, food processors may be able to reduce economic costs associated with foodborne illness outbreaks. Furthermore, effects on individual health and/or public health may be avoided or reduced by the deployment of the foodborne pathogen detection systems and associated methods described herein.

The foodborne pathogen detection systems and associated methods may also aid food processors in complying with food safety laws and regulations, such as those promulgated by government agencies such as the U.S. FDA.

FIG. 1 depicts an example foodborne pathogen detection environment 100 in some environments. The foodborne pathogen detection environment 100 includes food processing apparatuses 106A to 106N (referred to herein as a food processing apparatus 106 or food processing apparatuses 106), light intensity measuring apparatuses 102A to 102N (referred to herein as a light intensity measuring apparatus 102 or light intensity measuring apparatuses 102), a communication network 108, and a foodborne pathogen detection system 104. Although a single foodborne pathogen detection system 104 is depicted in FIG. 1, the foodborne pathogen detection environment 100 may include any number of foodborne pathogen detection systems 104. The foodborne pathogen detection environment 100 may also include other systems, apparatuses, devices, machines, and/or components not illustrated in FIG. 1, such as cleaning systems, water supply and water drain systems, and/or electrical and communication systems.

The food processing apparatus 106 may be or include any device or machine that processes food for human or animal consumption. For example, the food processing apparatus 106 may be a washing machine that washes fruits and vegetables such as leafy greens, apples, carrots, and the like using water. As another example, the food processing apparatus 106 may be a commercial spinner that dries washed lettuce and other vegetables, which produces water to be drained away. Other examples of food processing apparatuses 106 are within the scope of this disclosure. The food processing apparatus 106 may be or include any number of digital devices. Digital devices are discussed, for example, with reference to FIG. 12.

The light intensity measuring apparatus 102 may be or include any digital device. In one example, the light intensity measuring apparatus 102 may include one or more computers in communication with one or more spectrometers, such as the spectrometers discussed in the co-pending application U.S. patent application Ser. No. 18/173,050, filed on the same day and entitled "SYSTEMS AND METHODS FOR DETECTING PATHOGENS USING SPECTROMETER SCANS," which is incorporated in its entirety herein by reference. In another example, the light intensity measuring apparatus 102 may each be or include a different spectrometer, sensor, or detector capable of network communication. The light intensity measuring apparatus 102 may perform the functions of a spectrometer, such as the spectrometers discussed in the above-referenced co-pending application. For example, the light intensity measuring apparatus 102 may receive water samples, detect light that has passed through the water samples and measure multiple times intensities of wavelengths of the light, and transmit multiple sets of measured intensities to the foodborne pathogen detection system 104 for processing. In some embodiments, in addition to detecting and measuring intensities of wavelengths of light that has passed through the water samples, the light intensity measuring apparatus 102 may process the multiple sets of measured intensities, generate foodborne pathogen detection notifications, and provide the foodborne pathogen detection notifications.

The foodborne pathogen detection system 104 may be or include any number of digital devices and may be distinct from the light intensity measuring apparatuses 102. The foodborne pathogen detection system 104 may receive the multiple sets of measured intensities, process the multiple sets of measured intensities as described herein (e.g., with reference to FIG. 8), generate a foodborne pathogen detection notification, and provide the foodborne pathogen detection notification. In some embodiments, the foodborne pathogen detection system 104 provides the foodborne pathogen detection notification to the light intensity measuring apparatus 102.

The light intensity measuring apparatus 102 and/or the foodborne pathogen detection system 104 may, in the event of a positive foodborne pathogen detection notification, notify third party systems such as those operated by food processors, those operated by government agencies such as the U.S. FDA, and/or those operated by third parties approved by such government agencies. In such an event, the light intensity measuring apparatus 102 and/or the foodborne pathogen detection system 104 may also recommend further diagnostic analysis by government agencies or other third parties approved by the government agencies.

In some embodiments, communication network 108 represents one or more computer networks (for example, LANs, WANs, and/or the like). The communication network 108 may provide communication between any of the food processing apparatuses 106, any of the light intensity measuring apparatuses 102, and the foodborne pathogen detection system 104. In some implementations, the communication network 108 comprises computer devices, routers, cables, uses, and/or other network topologies. In some embodiments, the communication network 108 may be wired and/or wireless. In various embodiments, the communication network 108 may comprise the Internet, one or more networks that may be public, private, IP-based, non-IP based, and so forth.

Some embodiments described herein discuss performing spectral analysis on water samples (e.g., obtained from wash water), such as those obtained directly or indirectly from food processing apparatuses 106. It will be appreciated that the light intensity measuring apparatus 102 and/or the foodborne pathogen detection system 104 may perform spectral analysis on any food processing byproduct. Examples of food processing byproducts include, but are not limited to, water, wash water, oils, greases, animal blood, meat, and feces from animals such as cows, pigs, chickens. Furthermore, samples may be obtained by swabbing or otherwise sampling food processing equipment, surfaces, residues, or anything that comes into contact with food. Those of skill in the art will understand that food processing byproducts are not limited to the examples described herein.

Figure 2A:
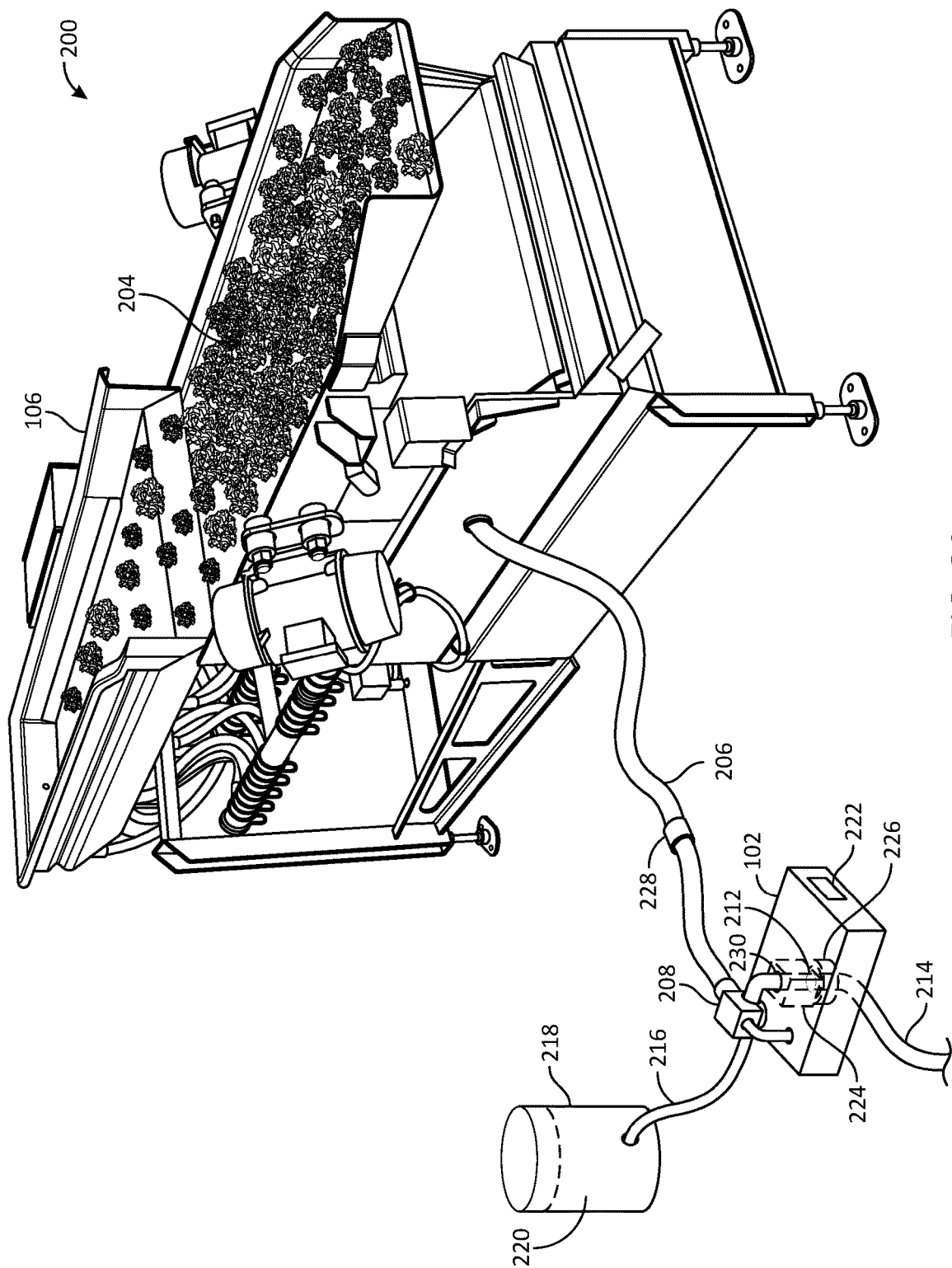
FIG. 2A depicts an example food processing environment in some embodiments.

FIG. 2A depicts an example food processing environment 200 in some embodiments. The food processing environment 200 includes a food processing apparatus 106, a cleaning fluid container 218, a light intensity measuring apparatus 102 coupled to both the food processing apparatus 106 and the cleaning fluid container 218, and various water supply and water draining components. The food processing apparatus 106 has pieces of produce 204, such as lettuce, on it to be washed. The light intensity measuring apparatus 102 may be positioned proximate to the food processing apparatus 106 and may be positioned on a support (e.g., a bench, not illustrated in FIG. 2A). The cleaning fluid container 218 may be positioned proximate to the light intensity measuring apparatus 102 and also may be positioned on the same support or a different support as the light intensity measuring apparatus 102 (e.g., a bench, also not illustrated in FIG. 2A).

The light intensity measuring apparatus 102 includes a supply valve 208. The supply valve 208 may be or include, for example, a solenoid valve, such as a three-way solenoid valve. The supply valve 208 is couplable to (and is depicted as coupled to) a water sample supply line 206 which is coupled to the food processing apparatus 106. The water sample supply line 206 includes a supply filter 228. The supply valve 208 is also couplable to (and is depicted as coupled to) to a cleaning fluid supply line 216 which is coupled to the cleaning fluid container 218, which contains cleaning fluid 220. The cleaning fluid container 218 may include sensors (not illustrated in FIG. 2A) that the light intensity measuring apparatus 102 uses to measure an amount of the cleaning fluid 220.

The light intensity measuring apparatus 102 is couplable to (and is depicted as coupled to) the food processing apparatus 106. The light intensity measuring apparatus 102 includes a chamber 224 which has a first opening 230 coupled to the supply valve 208 and a second opening 212 coupled to a drain valve 226. The drain valve 226 is coupled to a drain line 214. The light intensity measuring apparatus 102 also includes a display 222, which may be a touchscreen display, and may include other components not illustrated in FIG. 2A (e.g., input components such as buttons, status light-emitting diodes (LEDs) and the like). Although the water sample supply line 206, the drain line 214, and the cleaning fluid supply line 216 are depicted in FIG. 2A as flexible lines, each may be or include flexible, rigid or semi-rigid tubing or piping, such as copper pipes, PEX pipes, CPVC pipes, and the like.

In operation, the food processing apparatus 106 receives water from a water supply (not illustrated in FIG. 2A) and uses the water to wash the produce 204. Water drains from the food processing apparatus 106 via one or more drain lines (not illustrated in FIG. 2A) to which the water sample supply line 206 is coupled. The supply filter 228 filters any large particles (e.g., dirt, pieces of lettuce) in the water flowing through the water sample supply line 206. The light intensity measuring apparatus 102 opens the supply valve 208 to allow an appropriate amount of water (e.g., approximately 1 milliliter (ml) to approximately 2 ml, such as 1.25 ml) to flow through the water sample supply line 206 into the chamber 224 via the first opening 230 for sampling. As discussed with more reference to, e.g., FIG. 3, the light intensity measuring apparatus 102 generates light that passes through at least a portion of a water sample in the chamber. The light intensity measuring apparatus 102 detects and measures multiple times intensities of wavelengths of the light that has passed through the at least portion of the water sample. The light intensity measuring apparatus 102 provides the multiple sets of measured intensities to the foodborne pathogen detection system 104 for processing. The light intensity measuring apparatus 102 then opens the drain valve 226 to allow the water sample to drain out of the chamber 224 via the second opening 212 and into the drain line 214.

The light intensity measuring apparatus 102 then opens the supply valve 208 to allow an appropriate amount of cleaning fluid 220 (e.g., approximately 1 ml to approximately 2 ml, such as 1.25 ml) to flow from the cleaning fluid container 218 into the chamber 224 via the first opening 230. The light intensity measuring apparatus 102 causes a transducer (e.g., the transducer illustrated in FIG. 3) to move the chamber 224 to agitate the cleaning fluid 220 within the chamber 224. The light intensity measuring apparatus 102 then opens the drain valve 226 to allow the cleaning fluid to drain out of the chamber 224 via the second opening 212 and into the drain line 214. In this way, the light intensity measuring apparatus 102 cleans the chamber 224 so that the risk of false positives for subsequent water samples may be reduced.

Figure 2B:
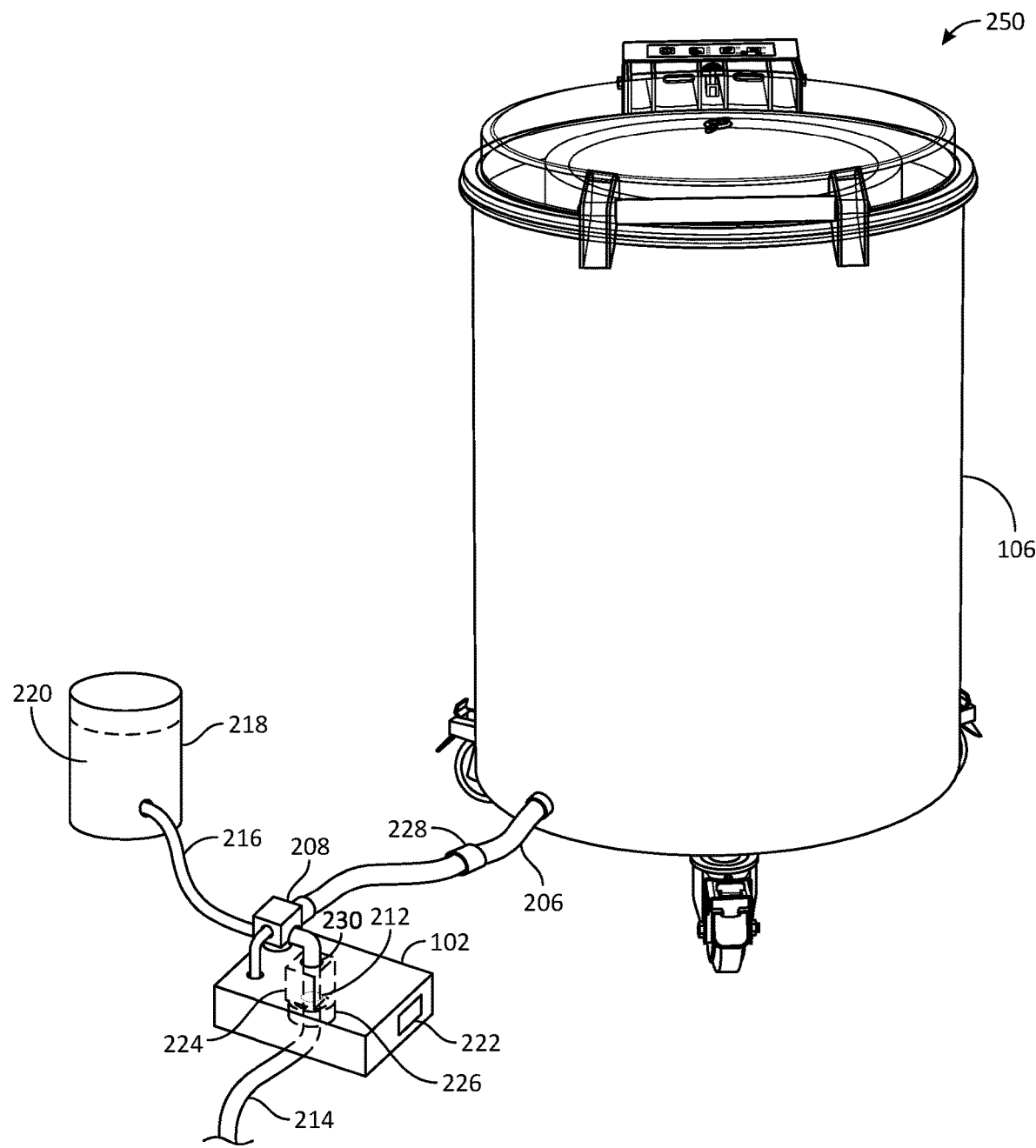
FIG. 2B depicts another example food processing environment in some embodiments.

FIG. 2B depicts another example food processing environment 250 in some embodiments. In the food processing environment 250, the food processing apparatus 106 is a salad spinner that may be used to dry wet lettuce or other wet produce. The food processing apparatus 106 produces water as it spins, which may drain via one or more drain lines (not illustrated in FIG. 2B) to which the water sample supply line 206 is coupled. Other like reference numerals in FIG. 2B refer to like elements in FIG. 2A and are not discussed with reference to FIG. 2B.

Figure 3:
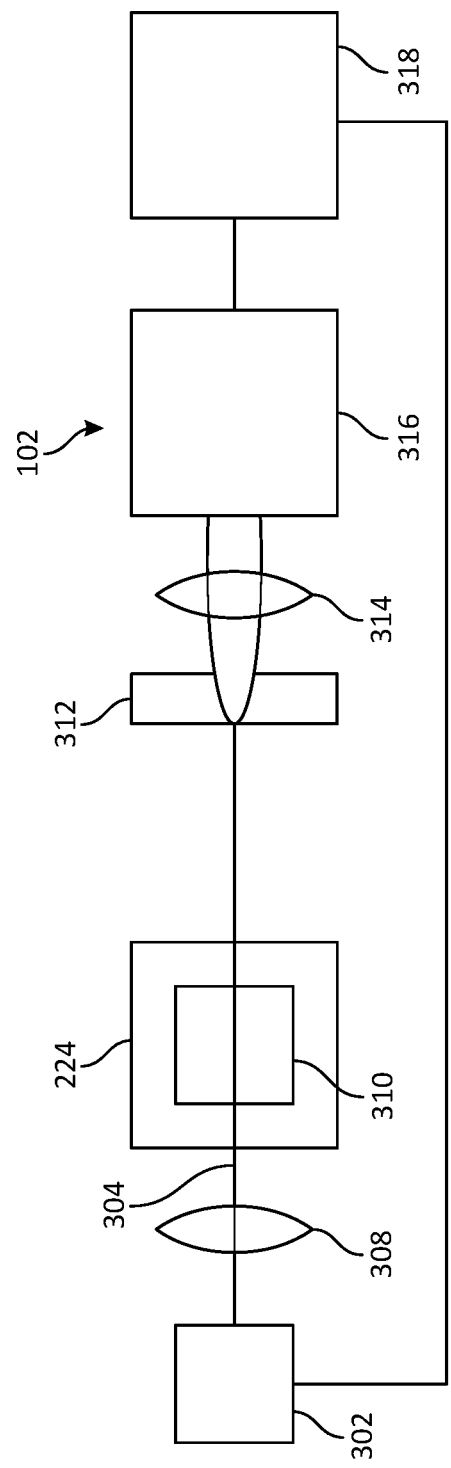
FIG. 3 depicts components of a light intensity measuring apparatus in some embodiments.

FIG. 3 depicts components of the light intensity measuring apparatus 102 in some embodiments. The light intensity measuring apparatus 102 includes a light source 302, a first lens 308, a chamber 224, a transducer 310, a diffuser 312, a second lens 314, a detector 316, and a controller 318. The light intensity measuring apparatus 102 may also include other components not illustrated in FIG. 3, such as a server (e.g., a virtual network computing server (VNC) server) that communicates with a client or viewer (e.g., a VNC viewer) on a separate digital device.

The light source 302 may be any source of light including, but not limited to, a tungsten-halogen bulb, a laser, an LED, or the like. The light source 302 may be controlled by the controller 318. In one example, the controller 318 may control the light source 302 to project any number of wavelengths. By controlling the light source 302, the controller 318 may correlate wavelengths to scattered patterns detected by the detector 316. Light generated by the light source 302 travels along light path 304 through the first lens 308, the chamber 224, the diffuser 312, and the second lens 314 before reaching the detector 316.

The first lens 308 may be any lens capable of collimating and/or focusing light from the light source 302 to the chamber 224. The chamber 224 may be or include any object for receiving a sample—such as a cuvette. In some embodiments, the chamber 224 is configured to receive fluids, such as water, wash water, oils, alcohols, vinegars, or other fluids. In some embodiments, the chamber 224 is configured to receive swabs, strips or other devices to which samples may be affixed. The transducer 310 is coupled to the chamber 224 and is configured to move the chamber 224. The transducer 310 may be, for example, an actuator.

The diffuser 312 may be any diversifier. In one example, the diffuser 312 may include crushed glass. It will be appreciated that the diffuser 312 may include any material(s) that allow for light to pass and may also include speckle, occlusions, or obstacles to scatter light. The diffuser 312 may be optional.

The second lens 314 may collimate or focus light received from the diffuser 312 (which may spread as a result of the scattering) before the light is received by the detector 316. In some embodiments, the second lens 314 may project a portion of the light that passes through the diffuser 312. For example, the second lens 314 may direct light that is scattered by one or more specific occlusions of the diffuser 312 towards the detector 316. In some embodiments, the second lens 314 may focus scattered light from a subset of occlusion and/or vortexes of the diffuser 312 towards the detector 316. In some embodiments, light from the areas of the diffuser 312 that is not being projected through the subset of occlusions may be ignored, blocked, or otherwise disregarded for pattern recognition and/or signal detection improvement.

The detector 316 may include a CMOS sensor, a CCD sensor, or other suitable sensor, such as InGaAs, PbS, and PbSe sensors. The detector 316 may have 2048 pixels. In some embodiments, the detector 316 has fewer than 2048 pixels (e.g., 1024 pixels). In some embodiments, the detector 316 has greater than 2048 pixels (e.g., 4096 pixels). Each pixel of the detector 316 may detect light of a particular wavelength. For example, the detector 316 may detect light in a range of wavelengths from approximately 150 nanometers (nm) to approximately 1350 nm, such as from approximately 146 nm (e.g., 145.93 nm) to approximately 1334 nm (e.g., 1334.05 nm). Accordingly, the range of wavelengths detected by the detector 316 includes wavelengths of ultraviolet (UV), visible (VIS), near-infrared (NIR) and infrared (IR) light. In some embodiments, the detector 316 may be a short-wave infrared (SWIR) detector, a mid-wave infrared (MWIR), or a long-wave infrared (LWIR) detector. In some embodiments, the wavelengths of light detected by the detector 316 include different ranges, such as different portions of the visible and/or invisible light spectrum.

Figure 4A:
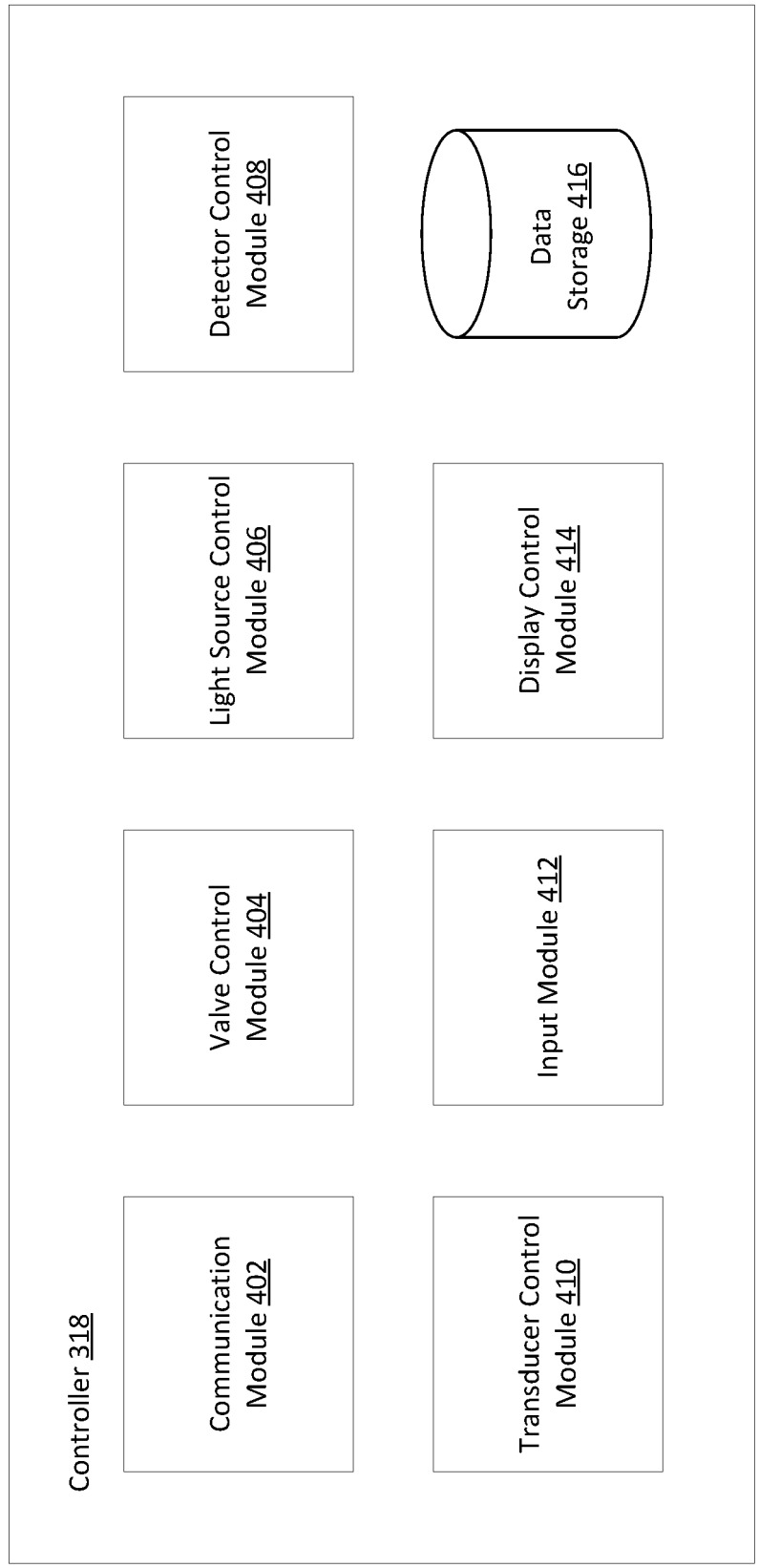
FIG. 4A is a block diagram of a controller of a light intensity measuring apparatus in some embodiments.

The controller 318 is communicably coupled to the light source 302 and the detector 316. FIG. 4A is a block diagram of the controller 318 in some embodiments. The controller 318 includes a communication module 402, a valve control module 404, a light source control module 406, a detector control module 408, a transducer control module 410, an input module 412, a display control module 414, and a data storage 416.

The communication module 402 may send and/or receive requests and/or data between the light intensity measuring apparatus 102 and any of the food processing apparatuses 106 or the foodborne pathogen detection system 104. The communication module 402 may receive requests and/or data from the food processing apparatuses 106 and/or the foodborne pathogen detection system 104. The communication module 402 may also send requests and/or data to the food processing apparatuses 106 and/or the foodborne pathogen detection system 104.

The valve control module 404 may control valves such as the supply valve 208 and the drain valve 226. The valve control module 404 may open the supply valve 208 to allow a sample, such as water or other liquid, or cleaning fluid to flow into the chamber 224. The valve control module 404 may open the drain valve 226 to allow the water sample or cleaning fluid to flow out of the chamber 224. The valve control module 404 may close the supply valve 208 and the drain valve 226.

The light source control module 406 may control the light source 302 to select wavelengths for measurements by detector 316. In some embodiments, the light source control module 406 does not control the light source 302 but rather receives wavelength information of light generated by the light source 302 (e.g., the light source 302 provides wavelength and any other information to the light source control module 406).

The detector control module 408 may control the detector 316 to detect and measure intensities of wavelengths of light after the light has passed through the sample in the chamber 224. The detector control module 408 may also receive intensity measurements from the detector 316. For example, the detector 316 may receive information or make measurements based on light received from the light source 302 (e.g., after being projected through chamber 224 and the diffuser 312). The detector 316 detects and measures multiple times intensities of wavelengths of light after the light has passed through at least a portion of the sample in the chamber 224. The detector 316 obtains multiple sets of measured intensities. In some embodiments, the detector 316 detects and measures intensities of wavelengths of light a single time.

The transducer control module 410 may control the transducer 310 to move the chamber 224. The transducer 310 may move the chamber 224 after it has been filled, completely or partially, with the sample. The transducer 310 may also move the chamber 224 after it has been filled, completely or partially, with the cleaning fluid 220 to clean the chamber 224.

The input module 412 may receive and process input to the light intensity measuring apparatus 102 received via input components such as buttons or the display 222.

The display control module 414 may display information on the display 222. Such information may include status information, foodborne pathogen detection notifications, and/or settings of the light intensity measuring apparatus 102.

The data storage 416 may include data stored, accessed, and/or modified by any of the modules of the light intensity measuring apparatus 102. The data storage 416 may include any number of data storage structures such as tables, databases, lists, and/or the like.

Figure 4B:
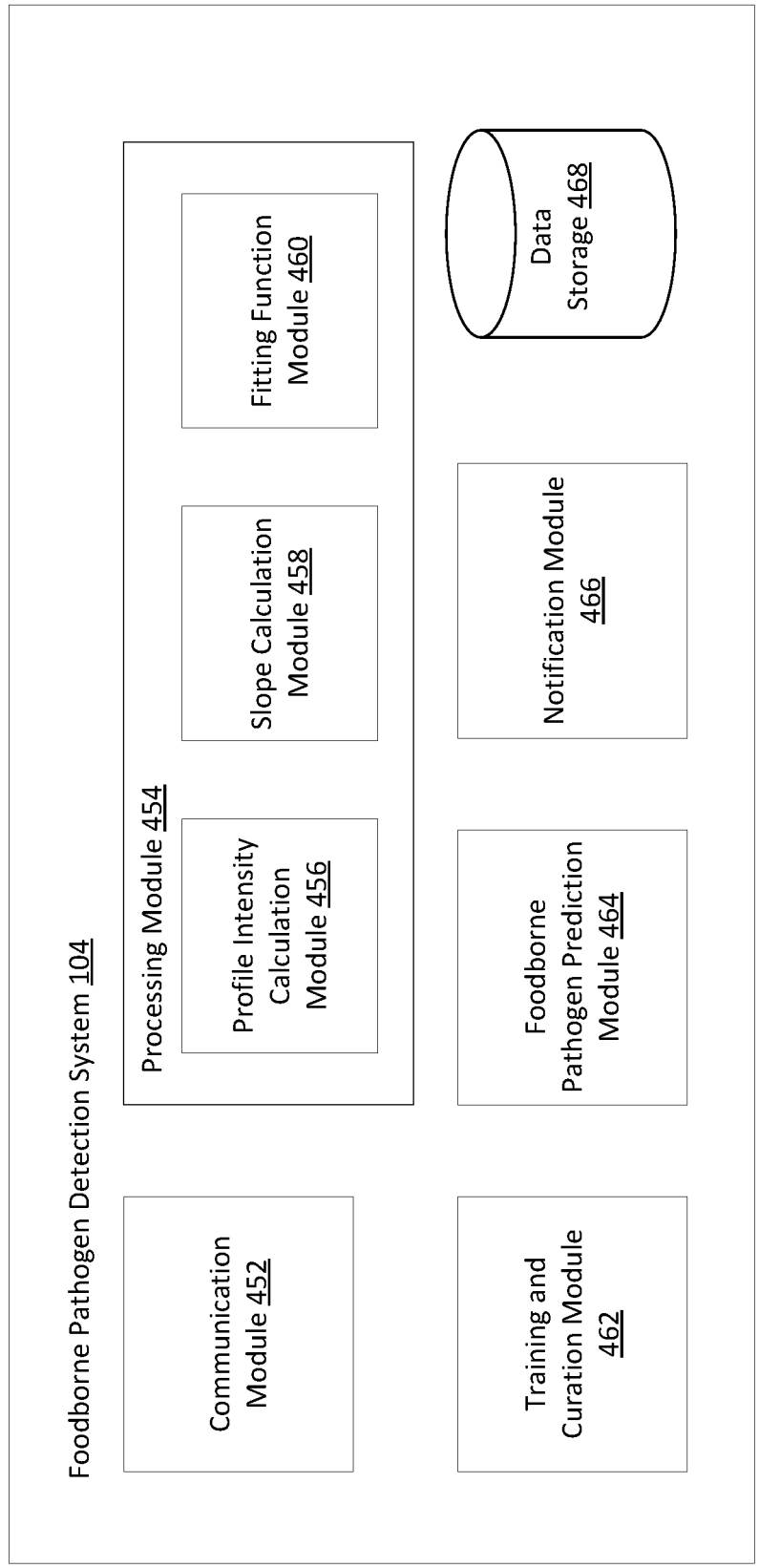
FIG. 4B is a block diagram of a foodborne pathogen detection system in some embodiments.

FIG. 4B depicts a block diagram of the foodborne pathogen detection system 104 in some embodiments. The foodborne pathogen detection system 104 includes a communication module 452, a processing module 454 that includes a profile intensity calculation module 456, a slope calculation module 458, and a fitting function module 460, a training and curation module 462, a foodborne pathogen prediction module 464, a notification module 466, and a data storage 468.

The communication module 452 may send and/or receive requests and/or data between the foodborne pathogen detection system 104 and any of the food processing apparatuses 106 or any of the light intensity measuring apparatuses 102. The communication module 452 may receive requests and/or data from the food processing apparatuses 106 and/or the light intensity measuring apparatuses 102. The communication module 452 may also send requests and/or data to the food processing apparatuses 106 and/or the light intensity measuring apparatuses 102.

The processing module 454 may process the multiple sets of measured intensities received from the light intensity measuring apparatuses 102 to obtain a set of values.

The profile intensity calculation module 456 may calculate profile intensities utilizing particular intensities of wavelengths of light included in the multiple sets of measured intensities of wavelengths of light received from the light intensity measuring apparatuses 102. The profile intensity calculation module 456 obtains multiple profile intensities for the sample.

The slope calculation module 458 may calculate slopes of the multiple profile intensities at multiple wavelengths to obtain a set of slopes.

The fitting function module 460 may apply a fitting function to the set of slopes to obtain a set of values.

The training and curation module 462 may train an artificial intelligence and/or machine learning system, (e.g., such as multiple sets of decision trees) to be applied and obtain results, either positive or negative, for foodborne pathogens for samples received by the light intensity measuring apparatuses 102.

The foodborne pathogen prediction module 464 may apply the trained artificial intelligence and/or machine learning system, such as the multiple sets of decision trees, to the set of values to obtain multiple results. A result indicates either a positive (a positive foodborne pathogen detection) or a negative (a negative foodborne pathogen detection) for a foodborne pathogen for the sample.

The notification module 466 may generate and provide notifications that include results of foodborne pathogen detections of the sample as well as other information, such as a confidence score. The notification module 466 may provide reports, alerts, and/or dashboards that include results, confidence scores, and/or other information. For example, the foodborne pathogen detection system 104 may track foodborne pathogen detections on particular food processing equipment as well as what food was processed on the food processing equipment. As another example, the foodborne pathogen detection system 104 may track foodborne pathogen detections in certain parts of a food processing facility as well as what food was processed in those certain parts. The pathogen detection system 104 may thus be able to identify food (e.g., particular lots or production runs) and recommend, via the notification module 466, that remedial action, such as quarantining food, recalling food, or other action, should be taken. The notification module 466 may optionally notify appropriate third parties (e.g., government agencies such as the U.S. FDA) of the detection of foodborne pathogens. The notification module 466 may, in some embodiments, prepare reports to aid in compliance with food safety laws and regulations.

The data storage 468 may include data stored, accessed, and/or modified by any of the modules of the foodborne pathogen detection system 104. The data storage 468 may include any number of data storage structures such as tables, databases, lists, and/or the like.

A module may be hardware, software, firmware, or any combination. For example, each module may include functions performed by dedicated hardware (e.g., an Application-Specific Integrated Circuit (ASIC), a Field Programmable Gate Array (FPGA), or the like), software, instructions maintained in ROM, and/or any combination. Software may be executed by one or more processors. Although a limited number of modules are depicted in FIGS. 4A and 4B, there may be any number of modules. Further, individual modules may perform any number of functions, including functions of multiple modules as shown herein.

Figure 5:
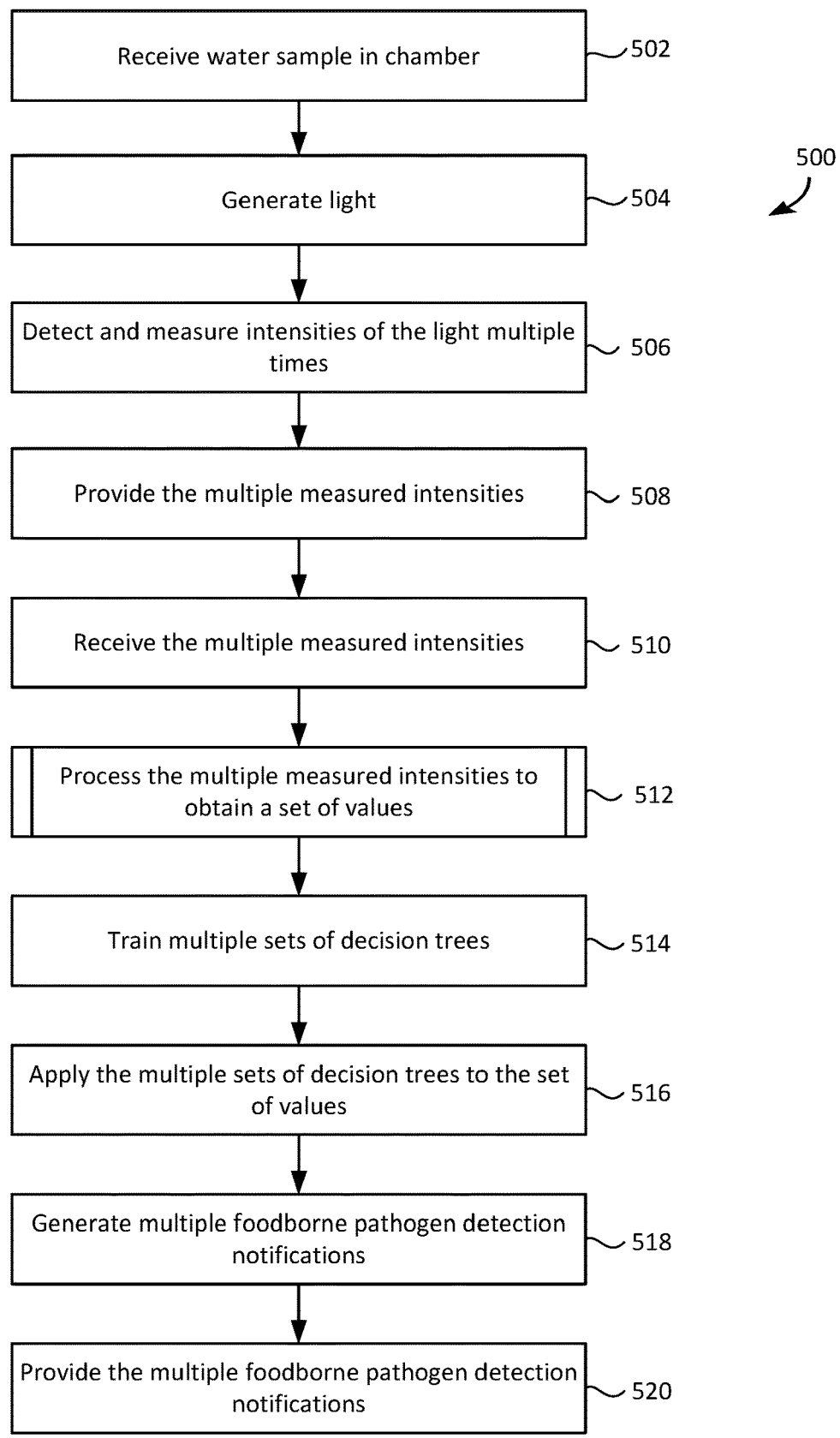
FIG. 5 is a flowchart showing a method for detecting foodborne pathogens in some embodiments.

FIG. 5 is a flowchart showing a method 500 for detecting foodborne pathogens in some embodiments. The method 500 is described with respect to a single water sample. The method 500 may be performed multiple times for multiple water samples.

The method 500 begins at step 502, where the light intensity measuring apparatus 102 receives a water sample in the chamber 224. The light intensity measuring apparatus 102 may receive water samples periodically (e.g., once an hour, once a day), based on lots of food being processed by the food processing apparatus 106, or on an as-needed or on-demand basis.

At step 504, the light source control module 406 controls the light source 302 to generate light which follows the light path 304 through at least a portion of the water sample in the chamber 224 to the detector 316. At step 506, the detector control module 408 controls the detector 316 to detect intensities of wavelengths of the light after the light has passed through at least a portion of the water sample. The detector control module 408 also controls the detector 316 to measure multiple times the intensities of wavelengths of the light that has passed through the at least portion of the water sample. In some embodiments, the detector 316 measures the intensities 1024 times, with a measurement performed at a generally equivalent amount of time after a previous measurement (e.g., several milliseconds). In some embodiments, the detector 316 may perform fewer (e.g., fewer than 1024, such as 512) or more (e.g., more than 1024, such as 2048) measurements.

At step 508, the communication module 402 provides the multiple sets of measured intensities, and at step 510 the communication module 452 of the foodborne pathogen detection system 104 receives the multiple sets of measured intensities. At step 512 the processing module 454 processes the multiple sets of measured intensities to obtain a set of values. The processing of the multiple sets of measured intensities by the processing module 454 is described in more detail with reference to, e.g., FIG. 8.

At step 514 the training and curation module 462 trains multiple sets of decision trees, a set of decision trees for each foodborne pathogen (e.g., *E. coli, salmonella, listeria*). In some embodiments, the training and curation module 462 utilizes an optimized distributed gradient boosting library, XGBoost. In some embodiments, the training and curation module 462 utilizes the following Python code to create each set of decision trees:

```
from xgboost import XGBClassifier
params = {"booster": "dart",
    "objective":"binary:logistic",
    "max_delta_step":1,
    "eval_metric":"auc",
    "eval_metric":"error",
    "n_estimators": 10000,
    "verbosity":0,
    "max_depth":20,
    "scale_pos_weight":100}
model = XGBClassifier(**params,use_label_encoder=False)
```

XGBClassifier may be understood as a single model that is an ensemble of 10,000 decision trees (the "n_estimators": 10000 parameter). In some embodiments, the training and curation module 462 may utilize additional parameters, such as "tree_method":"gpu_hist", "learning_rate":0.3, "early_stopping_rounds":15, and/or change values of parameters, such as setting the "max_depth" parameter value to be 35, the "scale_pos_weight" parameter value to be 10, and/or the value of the "n_estimators" parameter to be fewer than or greater than 10000 (to use fewer than or greater than 10,000 decision trees).

In some embodiments, the training and curation module 462 utilizes the following Python code to train each set of the multiple sets of decision trees:

```
model.fit(x_train, y_train, eval_set=[(x_test,y_test)],
    early_stopping_rounds=10)
```

In this code, x_train is training data, y_train is training labels, x_test is testing data, and y_test is testing labels. Both x_train and x_test are ground truth data. Both x_train and x_test may include both positive samples and negative samples. In some embodiments, both the x_train and x_test data are balanced, meaning that they include equal or generally equal numbers of positive samples and negative samples. In some embodiments, the x_train and x_test data may be imbalanced toward negative samples, meaning that they include more negative samples than positive samples. The training and curation module 462 may also use data sets that are imbalanced towards positive samples, meaning that they include more positive samples than negative samples.

In various embodiments, the training and curation module 462 may receive new ground truth data for a particular foodborne pathogen (e.g., new data that includes both positive samples and negative samples for the particular foodborne pathogen) and update the training data and the testing data and retrain the set of decision trees corresponding to the particular foodborne pathogen. For example, the training and curation module 462 may receive new ground truth data for *salmonella*. The training and curation module 462 may then update the training data and the testing data for *salmonella* and retrain the set of decision trees for *salmonella*. This may allow the foodborne pathogen detection system 104 to better detect *salmonella* in water samples. The foodborne pathogen detection system 104 may utilize similar processes for other foodborne pathogens such as *E. coli* and *listeria*. As a result, the models and/or AI architecture may be updated, improved, and/or curated based on new positive samples and new negative samples in the new ground truth data.

At step 516, the foodborne pathogen prediction module 464 applies the multiple sets of decision trees to the set of values to obtain multiple results. Each result indicates either a positive (a positive foodborne pathogen detection) or a negative (a negative foodborne pathogen detection) for a particular foodborne pathogen (e.g., *E. coli, salmonella, listeria*) for the water sample. In some embodiments, the foodborne pathogen prediction module 464 utilizes the following Python code to apply each set of trained decision trees to the set of values to obtain a result:

```
y_pred=model.predict(x_test)
```

In this code, y_pred is the result, and may be an integer that has value of either 0 or 1, with 0 indicating a negative result and 1 indicating a positive result. The foodborne pathogen prediction module 464 may further obtain a confidence score in applying a set of decision trees to the set of values. In some embodiments, the foodborne pathogen prediction module 464 utilizes the following Python code to obtain the confidence score:

```
y_score=model.predict_proba(x_test)
```

In this code, y_score is the confidence score, which may be a float that ranges between 0 and 1. The closer the value is to 0 the higher a degree of confidence that the result is negative, and the closer the value is to 1 the higher the degree of confidence that the result is positive. In some embodiments, the confidence score may be expressed as a percentage between 0% and 100%, inclusive.

At step 518, the notification module 466 generates multiple foodborne pathogen detection notifications that indicates the results for the water sample. A result may be either a positive foodborne pathogen detection or a negative foodborne pathogen detection for the particular foodborne pathogen (e.g., *E. coli, salmonella, listeria*). A foodborne pathogen detection notification may also indicate the confidence score in the foodborne pathogen detection notification.

At step 520, the notification module 466 provides the multiple foodborne pathogen detection notifications. The notification module 466 may provide the multiple foodborne pathogen detection notifications to the light intensity measuring apparatus 102 for display via the display 222, to the food processing apparatus 106, to devices of personnel of the entity operating the food processing apparatus 106, and/or to systems of the food processing apparatus 106.

In various embodiments, the notification module 466 generates reports, dashboards and/or other interfaces accessible via web browsers and/or device applications that provide information regarding foodborne pathogen detections, such as aggregated information about foodborne pathogen detections for a food processor. The notification module 466 may also aggregate and anonymize information from multiple food processors, such as foods processed, foodborne pathogens detected, locations, and the like. Such aggregated information may be of use to government agencies such as the U.S. FDA in determining the food or foods responsible for foodborne illness outbreaks.

In some embodiments, the training and curation module 462 trains a set of decision trees for the most common foodborne pathogens, such as *E. coli, salmonella*, and *listeria*. In some embodiments, the training and curation module 462 may train a set of decision trees for each of the following foodborne pathogens: norovirus, *salmonella* (non-typhoidal), *Clostridium perfringens, campylobacter, Staphylococcus aureus, Toxoplasma gondii, Escherichia coli* (*E. coli*), *Clostridium botulinum, cryptosporidium, Cyclospora*, hepatitis A virus, *shigella, Yersinia*, and *Listeria monocytogenes* (*listeria*). The foodborne pathogen prediction module 464 may apply one or more of the trained sets of decision trees to detect foodborne pathogens. Accordingly, the foodborne pathogen detection system 104 may provide panel detection and notification for various foodborne pathogens. One advantage of the foodborne pathogen detection system 104 is that it may provide results for such panel tests quickly (e.g., within seconds or minutes). Another advantage of the foodborne pathogen detection system 104 is that it obviates the need for sending samples to laboratories for test, which may reduce logistical issues and/or complexity.

In various embodiments, a machine learning and/or AI architecture may be utilized (e.g., random forest, statistical approaches, and/or the like) in addition to or as an alternative to the sets of decision tress discussed herein. The machine learning and/or AI architecture may utilize the features discussed herein to generate predictive models and/or make predictions. In various embodiments, a 1d or 2d convolutional neural network (CNN) may be used as a discriminator to identify measurements indicating foodborne pathogen contamination and non-foodborne pathogen contamination. In various embodiments, a neural network may be trained using measurements from the light intensity measuring apparatuses 102 as discussed herein. The neural network may also be trained using laboratory test results to confirm those foods, equipment, and/or surfaces that are contaminated and those that are not contaminated. The neural network may receive or generate a set of features based on the output (i.e., measurement results) of the light intensity measuring apparatuses 102. The neural network may then be tested to confirm predictions against known foodborne pathogen contamination and non-foodborne pathogen contamination results. In various embodiments, the models may treat waveforms generated by the light intensity measuring apparatuses 102 as a time series.

Figure 6:
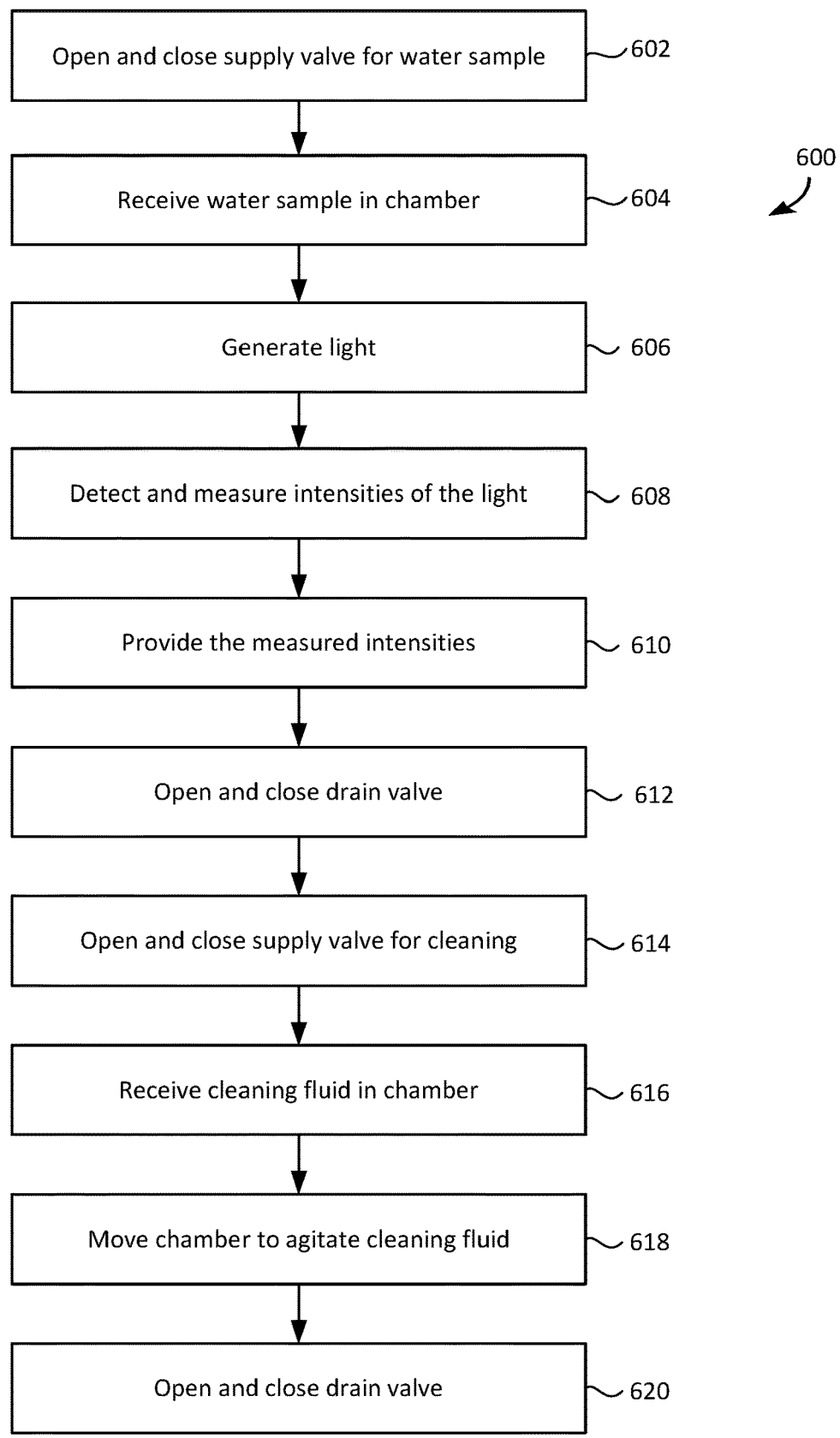
FIG. 6 is a flowchart showing a method for operating a light intensity measuring apparatus in some embodiments.

FIG. 6 is a flowchart showing a method 600 for operating a light intensity measuring apparatus 102 in some embodiments. The method 600 begins at step 602, where the valve control module 404 opens the supply valve 208 to allow an appropriate amount of water (e.g., approximately 5 ml to approximately 10 ml) to flow through the water sample supply line 206 into the chamber via the first opening 230, and then closes the supply valve 208. At step 604 the light intensity measuring apparatus 102 receives the water sample in the chamber 224.

At step 606 the light source control module 406 controls the light source 302 to generate light which follows the light path 304 through at least a portion of the sample in the chamber 224 to the detector 316. At step 608 the detector control module 408 controls the detector 316 to detect intensities of wavelengths of the light after the light has passed through at least a portion of the water sample. The detector control module 408 also controls the detector 316 to measure multiple times the intensities of wavelengths of the light that has passed through the at least portion of the water sample. At step 610, the communication module 402 provides the multiple sets of measured intensities. At step 612 the valve control module 404 opens the drain valve 226 to allow the water sample to drain out of the chamber 224 via the second opening 212 and through the drain line 214, and then closes the drain valve 226.

At step 614 the valve control module 404 opens the supply valve 208 to allow an appropriate amount of cleaning fluid 220 (e.g., approximately 5 ml to approximately 10 ml) to flow from the cleaning fluid container 218 to the chamber 224 via the first opening 230, and then closes the supply valve 208. At step 616 the light intensity measuring apparatus 102 receives the cleaning fluid 220 in the chamber 224. At step 618 the transducer control module 410 controls the transducer 310 to move the chamber 224 to agitate the cleaning fluid 220 within the chamber 224. At step 620 the valve control module 404 opens the drain valve 226 to allow the cleaning fluid to drain out of the chamber 224 via the second opening 212 through the drain line 214, and then closes the drain valve 226. In this way, the light intensity measuring apparatus 102 cleans the chamber 224 so that the risk of false positives for subsequent water samples may be reduced.

In some embodiments, if the light intensity measuring apparatus 102 or the foodborne pathogen detection system 104 detects a foodborne pathogen, the light intensity measuring apparatus 102 may not perform step 614 through step 620 of the method 600. The light intensity measuring apparatus 102 may not perform these steps because detection of a foodborne pathogen requires that personnel of the food processor operating the food processing apparatus 106 clean and sanitize the food processing apparatus 106 as well as the light intensity measuring apparatus 102 and associated equipment.

In various embodiments, the chamber 224 of the light intensity measuring apparatus 102 may be configured to receive a cuvette (or similar device) that contains the water sample. Personnel of the entity operating the food processing apparatus 106 may manually fill the cuvette with water from the food processing apparatus 106 and place the cuvette in the chamber 224. The light intensity measuring apparatus 102 may then perform step 606 through step 610 of the method 600. The light intensity measuring apparatus 102 may then indicate to the personnel (e.g., via the display 222) to remove the cuvette from the chamber 224.

Entities operating food processing facilities have their personnel clean the food processing apparatuses 106 and other equipment in the food processing facilities, such as after a production run and/or after a certain period of time. Typically, the personnel wash the food processing apparatuses 106 and other equipment with detergents and/or disinfectants, and then rinse the food processing apparatuses 106 and other equipment with water. At various points in this cleaning cycle, the personnel may fill the cuvette with water and place it in the chamber 224 of the light intensity measuring apparatus 102. Alternatively, the light intensity measuring apparatus 102 may be connected to drain lines that drain water and receive water samples from the drains. If a foodborne pathogen such as *E. coli, salmonella*, or *listeria* is detected, the personnel may perform another cleaning cycle to ensure that food processing apparatuses 106 and other equipment is fully cleaned. This may prevent or reduce the occurrence of contamination of food processed in subsequent production runs by the food processing apparatuses 106. The personnel may also quarantine the previously processed food to prevent it from being shipped out.

Figure 7:
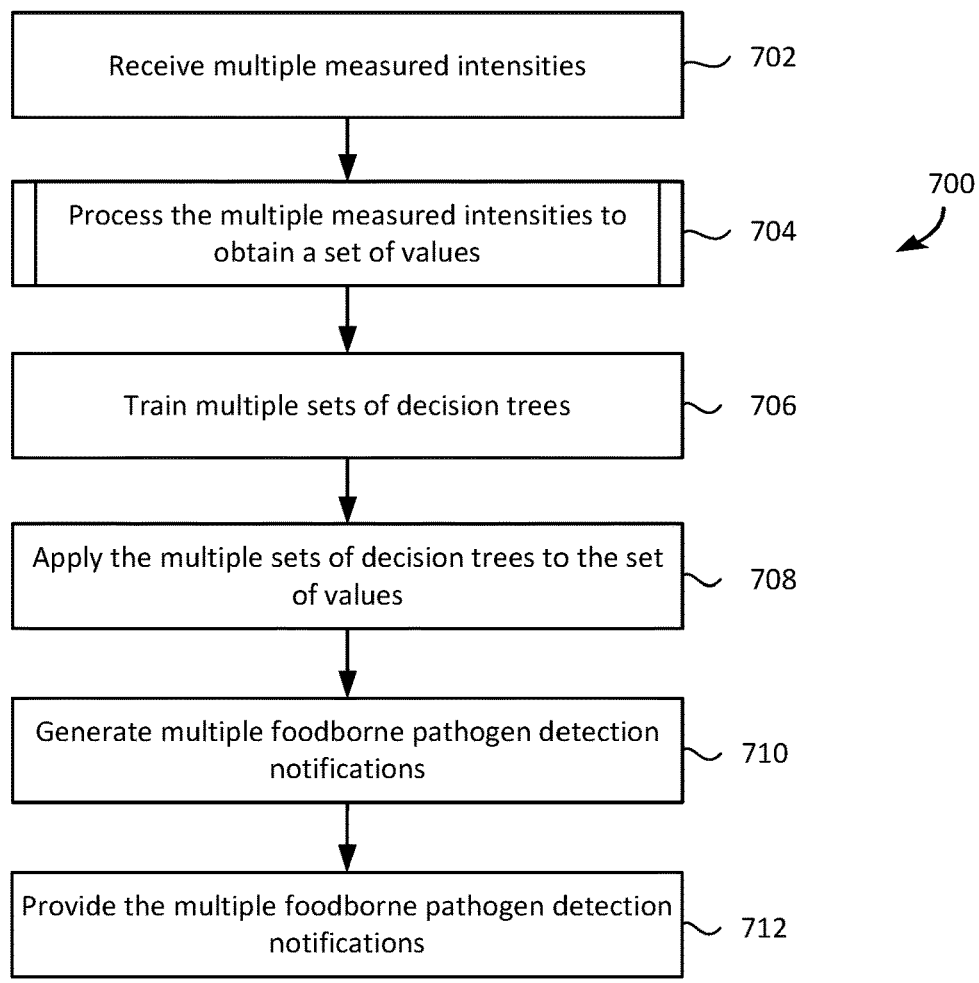
FIG. 7 is a flowchart showing a method for detecting foodborne pathogens in some embodiments.

FIG. 7 is a flowchart showing a method 700 for detecting foodborne pathogens in some embodiments. The foodborne pathogen detection system 104 may perform the method 700. The method 700 begins at step 702, where the communication module 452 receives the multiple sets of measured intensities from the communication module 402 of the light intensity measuring apparatus 102. At step 704 the processing module 454 processes the multiple sets of measured intensities to obtain a set of values. The processing of the multiple sets of measured intensities by the processing module 454 is described in more detail with reference to, e.g., FIG. 8.

At step 706 the training and curation module 462 trains multiple sets of decision trees, a set of decision trees for each foodborne pathogen (e.g., *E. coli, salmonella, listeria*). Step 706 may be generally similar to step 514 of the method 500 of FIG. 5.

At step 708 the foodborne pathogen prediction module 464 applies the multiple sets of decision trees to the set of values to obtain multiple results. Each result indicates either a positive (a positive foodborne pathogen detection) or a negative (a negative foodborne pathogen detection) for a particular foodborne pathogen (e.g., *E. coli, salmonella, listeria*) for the sample. Step 708 may be generally similar to step 516 of the method 500 of FIG. 5.

At step 710 the notification module 466 generates multiple foodborne pathogen detection notifications that indicates the results for the multiple foodborne pathogens for the sample. A result may be either a positive foodborne pathogen detection or a negative foodborne pathogen detection. A foodborne pathogen detection notification may also indicate the confidence score in the foodborne pathogen detection notification. Step 710 may be generally similar to step 518 of the method 500 of FIG. 5.

At step 712, the notification module 466 provides the multiple foodborne pathogen detection notifications. The notification module 466 may provide the multiple foodborne pathogen detection notifications to the light intensity measuring apparatus 102, to the food processing apparatus 106, to devices of personnel of the entity operating the food processing apparatus 106, and/or to systems of the food processing apparatus 106. Step 712 may be generally similar to step 520 of the method 500 of FIG. 5.

Figure 8:
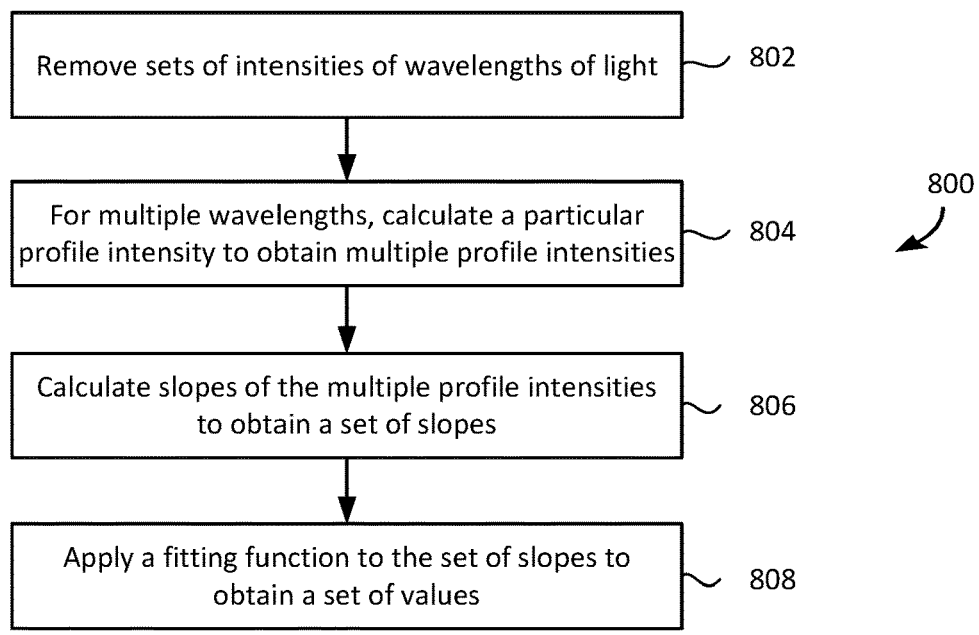
FIG. 8 is a flowchart showing a method for processing multiple sets of measured intensities of wavelengths in some embodiments.

FIG. 8 is a flowchart showing a method 800 for processing multiple sets of measured intensities in some embodiments. The foodborne pathogen detection system 104 may perform the method 800. The method 800 begins at step 802, where the training and curation module 462 removes one or more sets of intensities from the multiple sets of measured intensities. The training and curation module 462 removes from each of the multiple sets of measured intensities a set of intensities of wavelengths of light not associated with presences of one or more pathogens. Wavelengths associated with the presences of one or more pathogens are discussed with reference to, e.g., FIGS. 10A-B and FIGS. 11A-B. For example, the training and curation module 462 may receive an output from a spectrometer (or any device that performs spectral analysis) and may remove wavelengths that are not associated with a particular pathogen (e.g., *listeria*). The training and curation module 462 may subsequently receive a second output containing spectral analysis of the same sample (or a copy of the previous output prior to removing any wavelengths) and remove wavelengths that are not associated with a different pathogen (e.g., *salmonella*). The foodborne pathogen detection system 104 may then analyze the modified outputs for the different pathogens, respectively.

In some embodiments, the training and curation module 462 removes from each of the multiple sets of measured intensities a first set of intensities of wavelengths of light at a beginning of the range of wavelengths and a second set of intensities of wavelengths of light from the multiple sets of measured intensities at an end of the range of wavelengths. For example, the measured intensities may be of wavelengths of light that range from approximately 146 nm to approximately 1334 nm. The training and curation module 462 may remove intensities corresponding to approximately 12 nm from the beginning of the range of wavelengths and approximately 12 nm from the end of the range of wavelengths. Approximately 12 nm corresponds to approximately 20 pixels of the 2048 pixels of the detector 316. Accordingly, the training and curation module 462 may remove intensities detected and measured by the first approximately 20 pixels of the detector 316 and by the last approximately 20 pixels of the detector 316, which results in measured intensities corresponding to approximately 2008 pixels of the detector 316. In some embodiments, the training and curation module 462 may remove a different number of intensities from the beginning of the range of wavelengths of light from the multiple sets of measured intensities than from the end of the range of wavelengths of light from the multiple sets of measured intensities. In some embodiments, the training and curation module 462 does not remove any intensities from the multiple sets of measured intensities.

At step 804 the profile intensity calculation module 456, for multiple wavelengths of light in the range of wavelengths, calculates a particular profile intensity utilizing particular intensities of wavelengths of light included in the multiple sets of measured intensities to obtain multiple profile intensities. In some embodiments, the profile intensity calculation module 456, for multiple wavelengths of light in the range of wavelengths, calculates a particular average intensity utilizing particular intensities of wavelengths of light included in the multiple sets of measured intensities to obtain multiple average intensities. For example, the profile intensity calculation module 456 may take the intensity of light measured at a particular pixel of the detector (e.g., pixel index 100) of each of the 1024 scans, sum the 1024 intensities of light measured at the particular pixel, and then average the summed intensities to obtain a particular average intensity. The profile intensity calculation module 456 may do this for each pixel index (e.g., from pixel index 20 to pixel index 2027) to obtain 2008 particular average intensities. As pixel indices map to wavelengths, the profile intensity calculation module 456 may obtain 2008 particular average intensities for wavelengths ranging from approximately 158 nm to approximately 1322 nm. In some embodiments, the profile intensity calculation module 456 calculates particular profile intensities using other techniques (e.g., using weighted averages, medians).

At step 806 the slope calculation module 458 calculates slopes of the multiple profile intensities at multiple wavelengths to obtain a set of slopes. The slope calculation module 458 calculates a slope by dividing the difference in measured intensities of light between successive pixels by the difference in pixel indices. For example, the slope calculation module 458 calculates the slope at pixel index 20 by dividing the difference in measured intensities of light of pixel index 21 and pixel index 20 by one. The slope calculation module 458 performs this calculation at each pixel index, thereby obtaining a set of slopes. In some embodiments, the slope calculation module 458 calculates a slope by dividing the difference in intensities between successive pixels by the difference in wavelengths at those pixel indices. In some embodiments, the slope calculation module 458 calculates a slope by calculating the difference in measured intensities of light between successive pixels, without dividing the difference by any value.

At step 808, the fitting function module 460 applies a fitting function to the set of slopes to obtain a set of values. In some embodiments, the fitting function module 460 applies a smoothing filter, such as a Savitzky-Golay filter utilizing a second-order polynomial, to the set of slopes to obtain the set of values. In some embodiments, the Savitzky-Golay filter utilizes a window having a size of 151. The fitting function module 460 may apply a Savitzky-Golay filter utilizing polynomials of other orders and/or of other window sizes. In some embodiments, the fitting function module 460 applies a rolling average to the set of slopes utilizing a window size of 10 and a slide value of 1. The fitting function module 460 may apply a rolling average utilizing other windows of other sizes and/or other slide values. In some embodiments, the fitting function module 460 applies other fitting functions and/or signal processing techniques to smooth out the set of slopes and/or reduce noise.

In some embodiments, the light intensity measuring apparatus 102 performs the method 700 of FIG. 7 and/or the method 800 of FIG. 8. In such embodiments, the light intensity measuring apparatus 102 may include the processing module 454, which may include the profile intensity calculation module 456, the slope calculation module 458 and the fitting function module 460, the training and curation module 462, the foodborne pathogen prediction module 464, and the notification module 466.

Figure 9A:
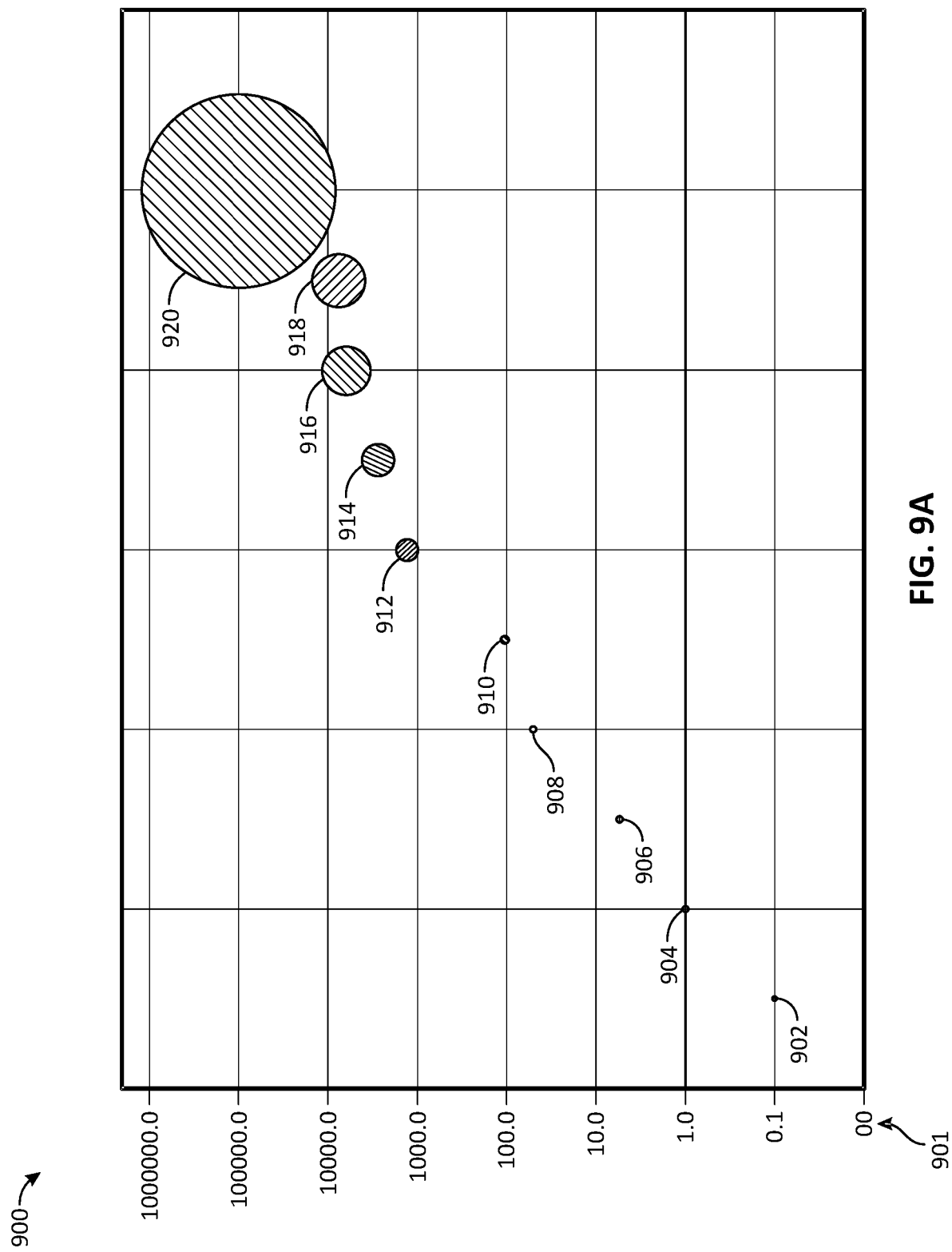
FIG. 9A is a chart depicting average sizes of various particles or items.

FIG. 9A is a chart 900 depicting average sizes of various particles or items. The chart 900 has a y-axis 901 in logarithmic scale of sizes in nanometers (nm). The chart 900 depicts an atom 902 (average size 0.1 nm), a small molecule 904 (average size 1.0 nm), a protein 906 (average size 6 nm), a nanoparticle 908 (average size 51 nm), and a virus virion 910 (average size 105 nm). The chart 900 further depicts particulate matter 912 (average size 1300 nm), a bacterium 914 (average size 2750 nm), a dust particle 916 (average size 6250 nm), a respiratory droplet 918 (average size 7500 nm), and the thickness of paper 920 (average size 100,000 nm).

Figure 9B:
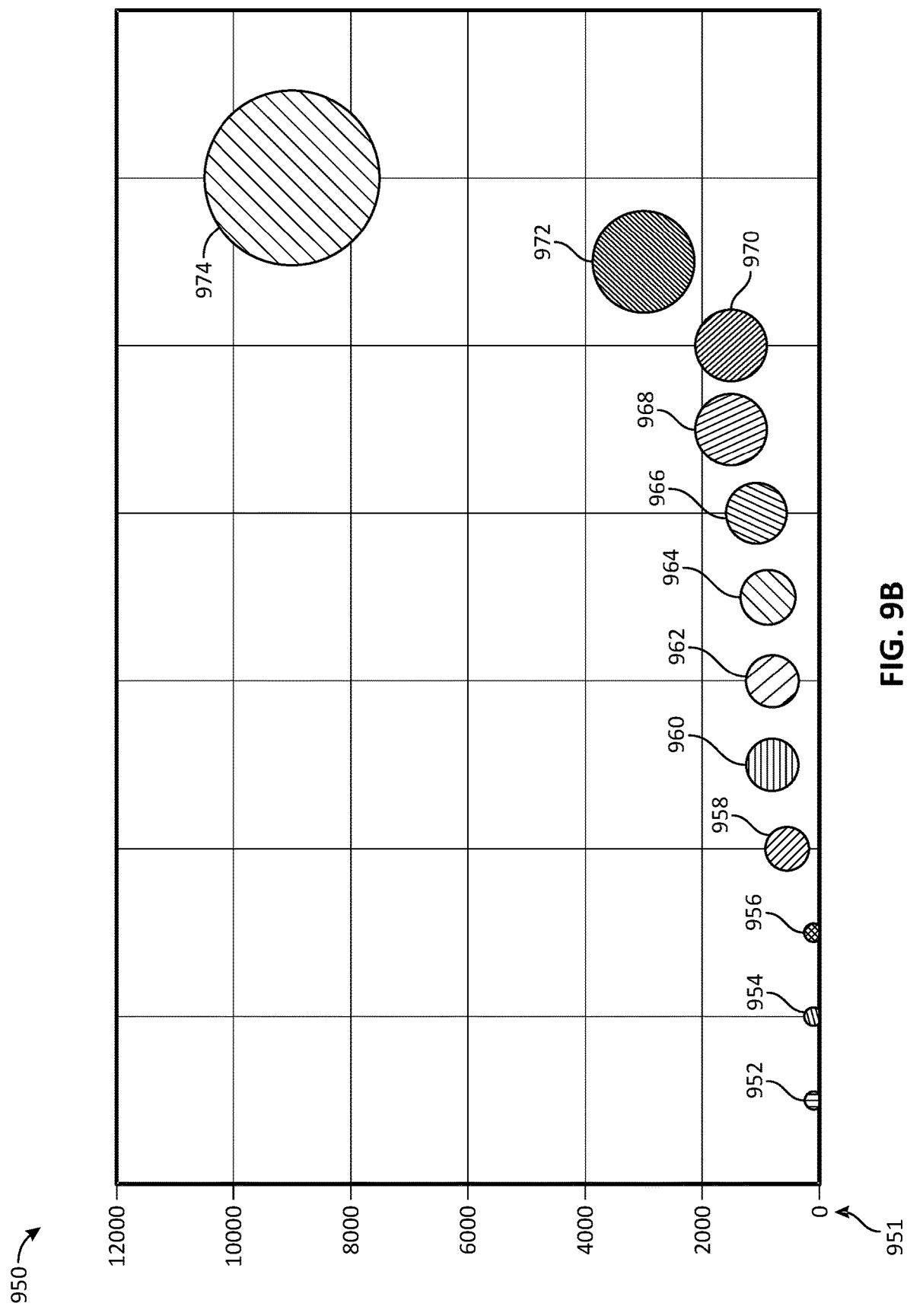
FIG. 9B is a chart depicting average sizes of various pathogens.

FIG. 9B is a chart 950 depicting average sizes of various pathogens. The chart 950 has a y-axis 951 in linear scale of sizes in nanometers (nm). The chart 950 depicts a SARS-CoV-2 virion 952 (average size 95 nm), a human immunodeficiency virus (HIV) virion 954 (average size 100 nm), an influenza A virus virion 956 (average size 100 nm), a *Chlamydia trachomatis* bacterium 958 (average size 550 nm), and a *Streptococcus* (Group A) bacterium 960 (average size 800 nm). The chart 950 further depicts a *Neisseria gonorrhoeae* bacterium 962 (average size 800 nm), a *Streptococcus pneumoniae* bacterium 964 (average size 875 nm), a *salmonella* bacterium 966 (average size 1068 nm), an *Escherichia coli* (*E. coli*) bacterium 968 (average size 1500 nm), a Pithovirus virus virion 970 (average size 1500 nm), a tuberculosis bacterium 972 (average size 3000 nm) and a *cyclospora* parasite 974 (average size 9000 nm).

Figure 10A:
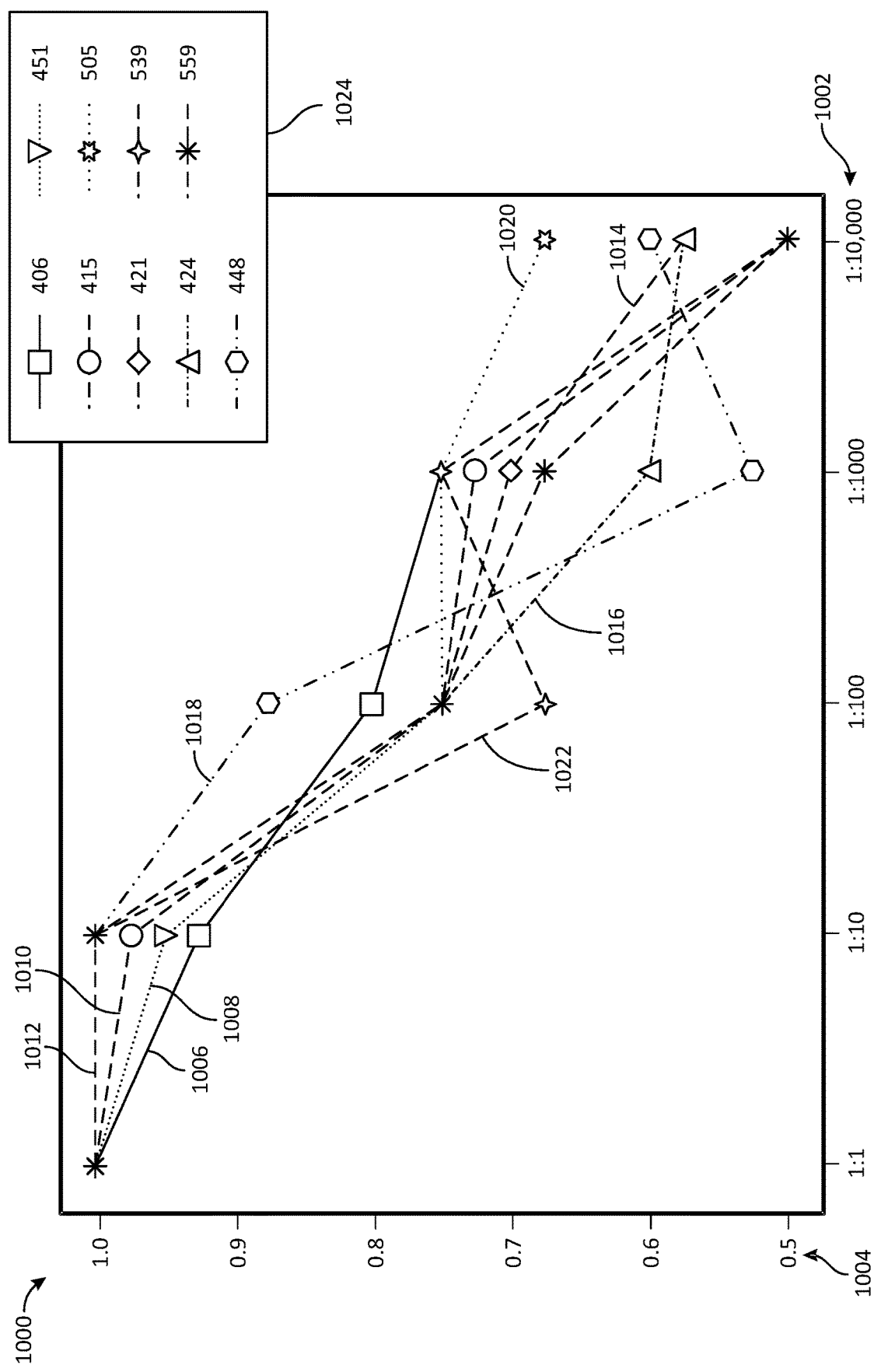
FIG. 10A is a graph depicting accuracies of various wavelengths in detecting *Escherichia coli* (*E. coli*) across five dilutions by a foodborne pathogen detection system in some embodiments.

FIG. 10A is a graph 1000 depicting accuracies of various wavelengths in detecting *Escherichia coli* (*E. coli*) across five dilutions by the foodborne pathogen detection system 104 in some embodiments. The graph 1000 has an x-axis 1002 for the dilution ratio (ratio of pathogen to water or other neutral medium) in logarithmic scale and a y-axis 1004 for the accuracy between 0 and 1 (with 0 corresponding to 0% accuracy and 1 corresponding to 100% accuracy). The graph 1000 includes a legend 1024 that indicates the various wavelengths in nanometers (nm). The wavelengths in the legend 1024 may be associated with a presence of *E. coli* in a sample. Wavelengths other than those in the legend 1024 may not be associated with the presence of *E. coli* in a sample. However, wavelengths other than those in the legend 1024 may also be associated with the presence of *E. coli* in a sample. Line 1006 in the graph 1000 shows the accuracy of wavelength 406 nm. Line 1008 in the graph 1000 shows the accuracy of wavelength 451 nm. Line 1010 in the graph 1000 shows the accuracy of wavelength 415 nm. Line 1012 in the graph 1000 shows the accuracy of wavelength 559 nm. Line 1014 in the graph 1000 shows the accuracy of wavelength 421 nm. Line 1016 in the graph 1000 shows the accuracy of wavelength 424 nm. Line 1018 in the graph 1000 shows the accuracy of wavelength 448 nm. Line 1020 in the graph 1000 shows the accuracy of wavelength 505 nm. Line 1022 in the graph 1000 shows the accuracy of wavelength 538 nm.

Figure 10B:
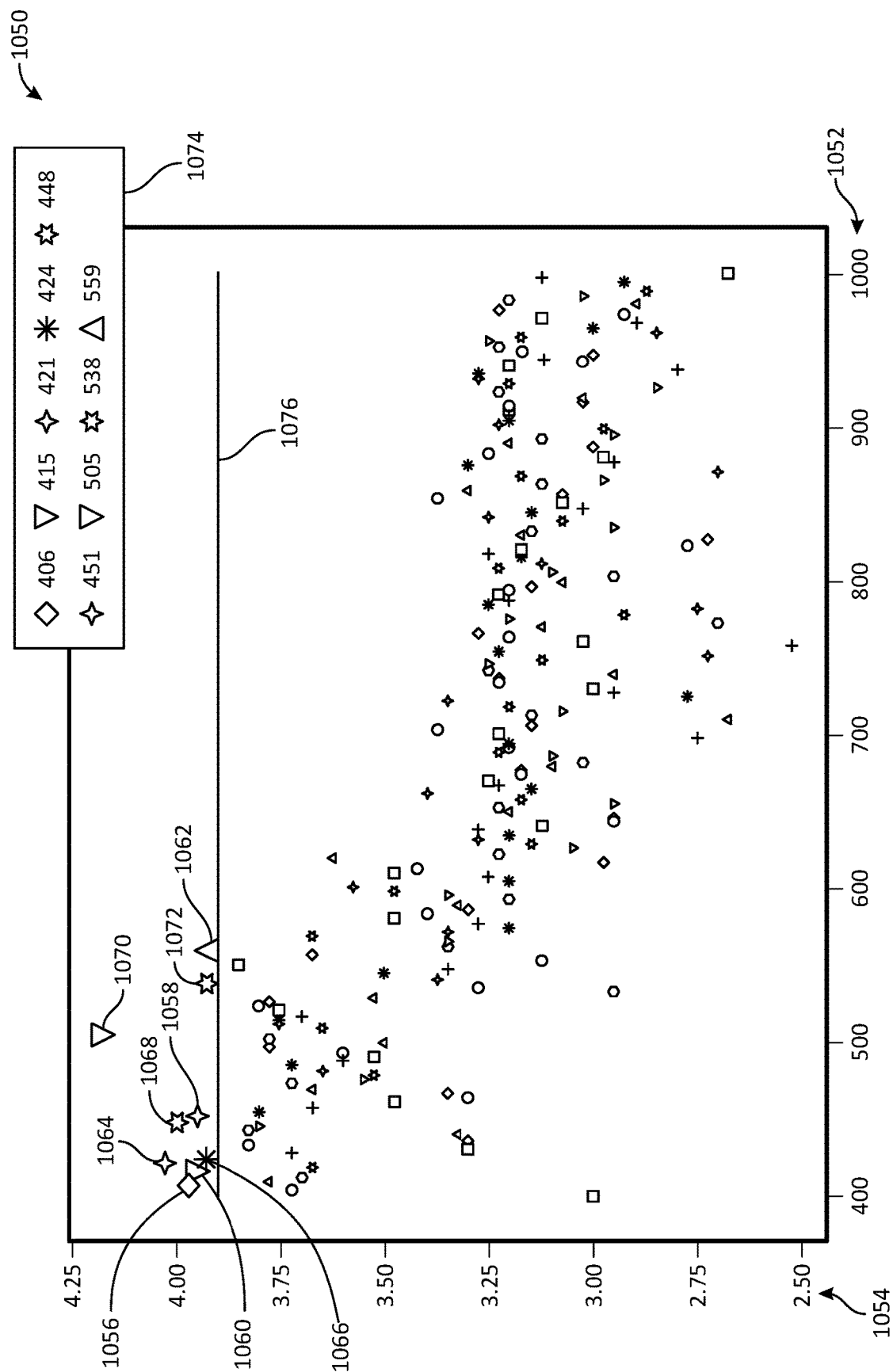
FIG. 10B is a graph depicting a sum of accuracies across all five dilutions by various wavelengths in detecting *Escherichia coli* (*E. coli*) across multiple dilutions by a foodborne pathogen detection system in some embodiments.

FIG. 10B is a graph 1050 depicting a sum of accuracies across all five dilutions by various wavelengths in detecting *Escherichia coli* (*E. coli*) across multiple dilutions by the foodborne pathogen detection system 104 in some embodiments. The graph 1050 has an x-axis 1052 for wavelengths (in nm) and a y-axis 1054 for a sum of accuracies across all five dilutions (1:1, 1:10, 1:100, 1:1000, and 1:10,000). The graph 1050 includes a legend 1074 that indicates the various wavelengths in nanometers (nm). The wavelengths in the legend 1074 may be associated with a presence of *E. coli* in a sample. Wavelengths other than those in the legend 1074 may not be associated with the presence of *E. coli* in a sample. However, wavelengths other than those in the legend 1074 may also be associated with the presence of *E. coli* in a sample. There are certain wavelengths whose sum of accuracies across all five dilutions exceeds a threshold indicated by line 1076. Point 1056 is the sum of accuracies across all five dilutions of wavelength 406 nm. Point 1058 is the sum of accuracies across all five dilutions of wavelength 451 nm. Point 1060 is the sum of accuracies across all five dilutions of wavelength 415 nm. Point 1062 is the sum of accuracies across all five dilutions of wavelength 559. Point 1064 is the sum of accuracies across all five dilutions of wavelength 421 nm. Point 1066 is the sum of accuracies across all five dilutions of wavelength 424 nm. Point 1068 is the sum of accuracies across all five dilutions of wavelength 448 nm. Point 1070 is the sum of accuracies across all five dilutions of wavelength 505 nm. Point 1072 is the sum of accuracies across all five dilutions of wavelength 538 nm.

Figure 11A:
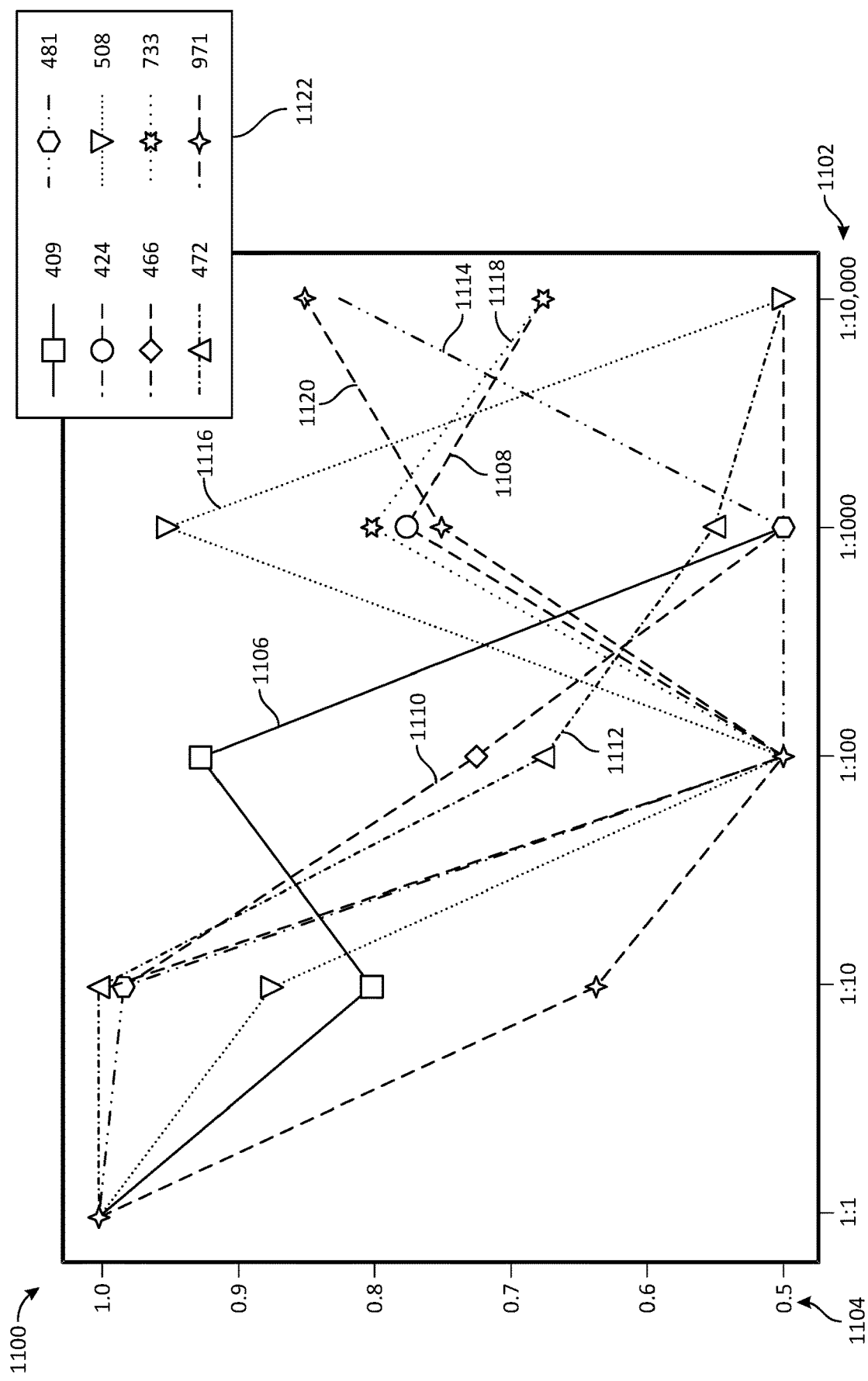
FIG. 11A is a graph depicting accuracies of various wavelengths in detecting *salmonella* across five dilutions by a foodborne pathogen detection system in some embodiments.

FIG. 11A is a graph 1100 depicting accuracies of various wavelengths in detecting *salmonella* across five dilutions by the foodborne pathogen detection system 104 in some embodiments. The graph 1100 has an x-axis 1102 for the dilution ratio (ratio of pathogen to water or other neutral medium) in logarithmic scale and a y-axis 1104 for the accuracy between 0 and 1 (with 0 corresponding to 0% accuracy and 1 corresponding to 100% accuracy). The graph 1100 includes a legend 1122 that indicates the various wavelengths in nanometers (nm). The wavelengths in the legend 1122 may be associated with a presence of *salmonella* in a sample. Wavelengths other than those in the legend 1122 may not be associated with the presence of *salmonella* in a sample. However, wavelengths other than those in the legend 1122 may also be associated with the presence of *salmonella* in a sample. Line 1106 in the graph 1100 shows the accuracy of wavelength 409 nm. Line 1108 in the graph 1100 shows the accuracy of wavelength 424 nm. Line 1110 in the graph 1100 shows the accuracy of wavelength 466 nm. Line 1112 in the graph 1100 shows the accuracy of wavelength 472 nm. Line 1114 in the graph 1100 shows the accuracy of wavelength 418 nm. Line 1116 in the graph 1100 shows the accuracy of wavelength 508 nm. Line 1118 in the graph 1100 shows the accuracy of wavelength 733 nm. Line 1120 in the graph 1100 shows the accuracy of wavelength 971 nm.

Figure 11B:
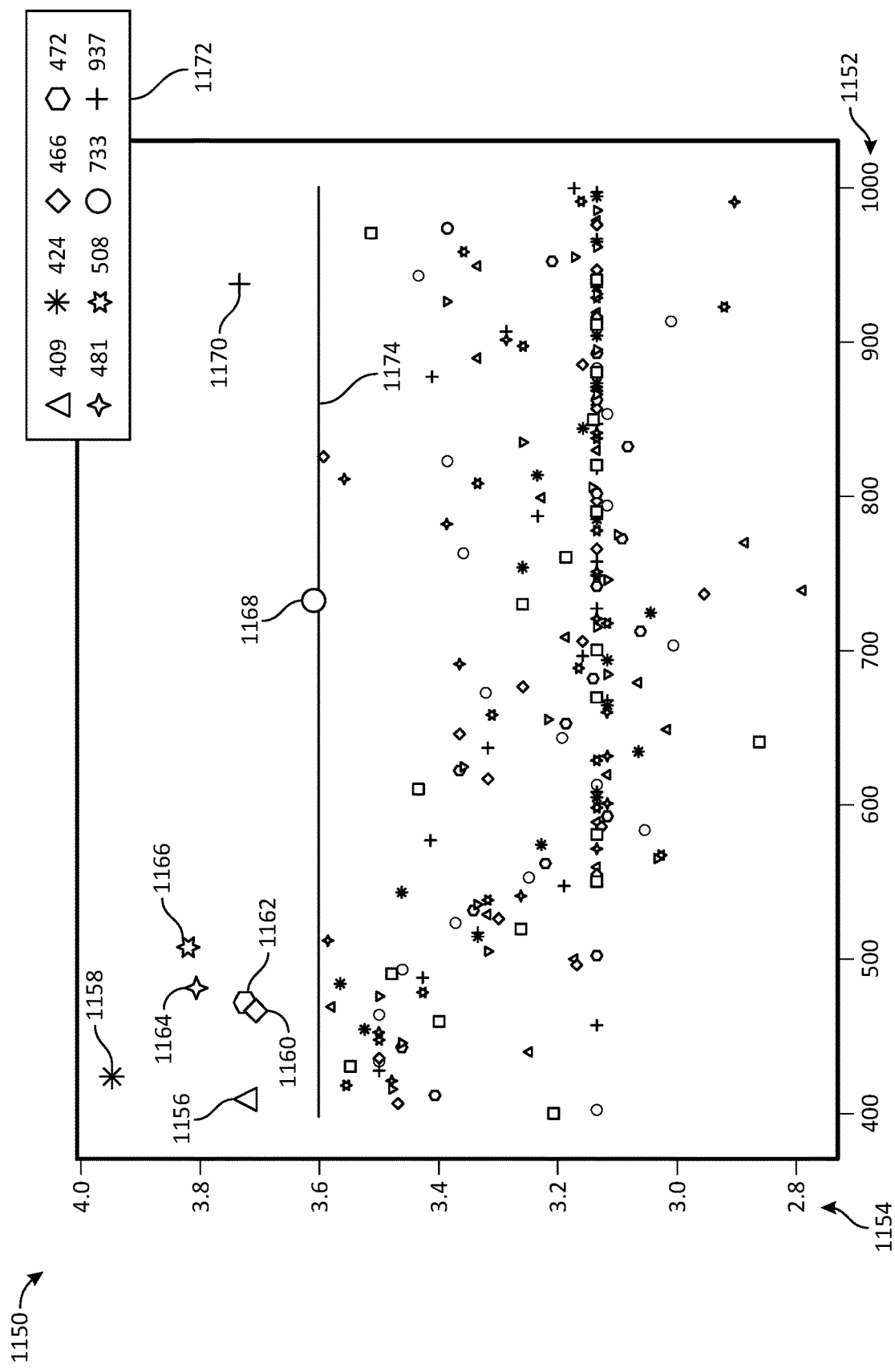
FIG. 11B is a graph depicting a sum of accuracies across all five dilutions by various wavelengths in detecting *salmonella* across multiple dilutions by a foodborne pathogen detection system in some embodiments.

FIG. 11B is a graph 1150 depicting a sum of accuracies across all five dilutions by various wavelengths in detecting *salmonella* across multiple dilutions by the foodborne pathogen detection system 104 in some embodiments. The graph 1150 has an x-axis 1152 for wavelengths (in nm) and a y-axis 1154 for a sum of accuracies across all five dilutions (1:1, 1:10, 1:100, 1:1000, and 1:10,000). The graph 1150 includes a legend 1172 that indicates the various wavelengths in nanometers (nm). The wavelengths in the legend 1172 may be associated with a presence of *salmonella* in a sample. Wavelengths other than those in the legend 1172 may not be associated with the presence of *salmonella* in a sample. However, wavelengths other than those in the legend 1172 may also be associated with the presence of *salmonella* in a sample. There are certain wavelengths whose sum of accuracies across all five dilutions exceeds a threshold indicated by line 1174. Point 1156 is the sum of accuracies across all five dilutions of wavelength 409 nm. Point 1158 is the sum of accuracies across all five dilutions of wavelength 424 nm. Point 1160 is the sum of accuracies across all five dilutions of wavelength 466 nm. Point 1162 is the sum of accuracies across all five dilutions of wavelength 472. Point 1164 is the sum of accuracies across all five dilutions of wavelength 481 nm. Point 1166 is the sum of accuracies across all five dilutions of wavelength 508 nm. Point 1168 is the sum of accuracies across all five dilutions of wavelength 733 nm. Point 1170 is the sum of accuracies across all five dilutions of wavelength 937 nm.

Figure 12:
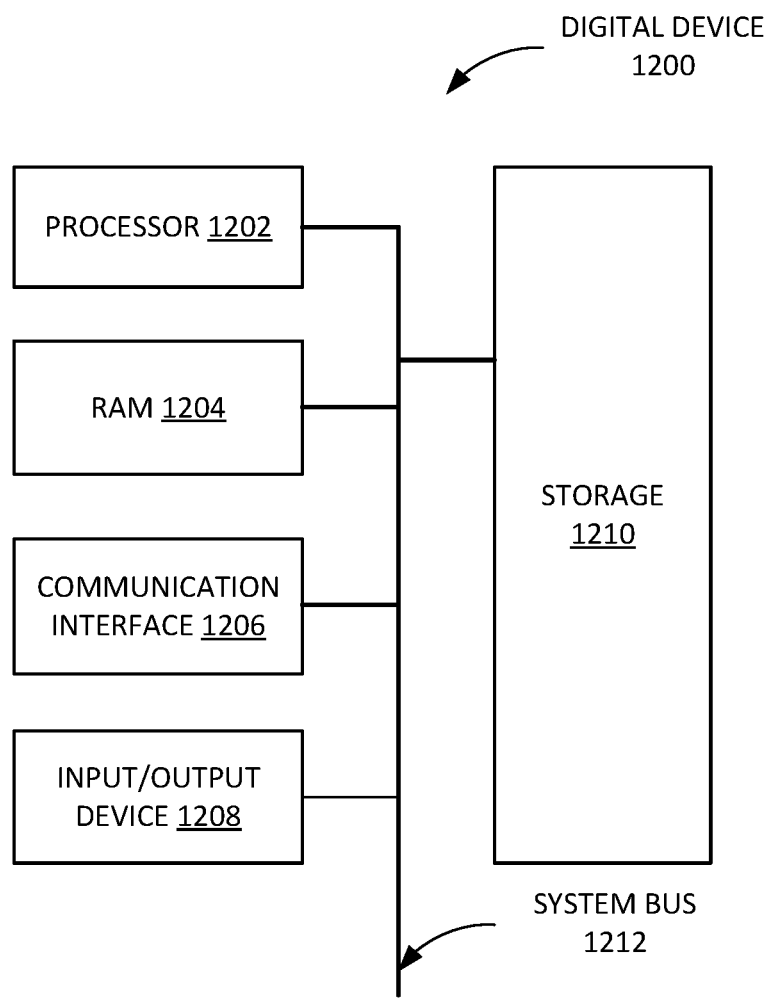
FIG. 12 depicts a block diagram of an example digital device in some embodiments.

FIG. 12 depicts a block diagram of an example digital device 1200 according to some embodiments. Digital device 1200 is shown in the form of a general-purpose computing device. Digital device 1200 includes at least one processor 1202, RAM 1204, communication interface 1206, input/ output device 1208, storage 1210, and a system bus 1212 that couples various system components including storage 1210 to the at least one processor 1202. A system, such as a computing system, may be or include one or more digital devices 1200.

System bus 1212 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Digital device 1200 typically includes a variety of computer system readable media, such as computer system readable storage media. Such media may be any available media that is accessible by the light intensity measuring apparatuses 102 and/or the foodborne pathogen detection system 104 and it includes both volatile and nonvolatile media, removable and non-removable media.

In some embodiments, the at least one processor 1202 is configured to execute executable instructions (for example, programs). In some embodiments, the at least one processor 1202 comprises circuitry or any processor capable of processing the executable instructions.

In some embodiments, RAM 1204 stores programs and/or data. In various embodiments, working data is stored within RAM 1204. The data within RAM 1204 may be cleared or ultimately transferred to storage 1210, such as prior to reset and/or powering down the digital device 1200.

In some embodiments, digital device 1200 is coupled to a network via communication interface 1206. Still yet, the light intensity measuring apparatuses 102 and/or the foodborne pathogen detection system 104 can communicate with one or more networks such as a local area network (LAN), a general wide area network (WAN), and/or a public network (for example, the Internet).

In some embodiments, input/output device 1208 is any device that inputs data (for example, mouse, keyboard, stylus, sensors, etc.) or outputs data (for example, speaker, display, virtual reality headset).

In some embodiments, storage 1210 can include computer system readable media in the form of non-volatile memory, such as read only memory (ROM), programmable read only memory (PROM), solid-state drives (SSD), flash memory, and/or cache memory. Storage 1210 may further include other removable/non-removable, volatile/non-volatile computer system storage media. By way of example only, storage 1210 can be provided for reading from and writing to a non-removable, non-volatile magnetic media. The storage 1210 may include a non-transitory computer-readable medium, or multiple non-transitory computer-readable media, which stores programs or applications for performing functions such as those described herein with reference to, for example, FIGS. 4A and 4B. Although not shown, a magnetic disk drive for reading from and writing to a removable, non-volatile magnetic disk (for example, a "floppy disk"), and an optical disk drive for reading from or writing to a removable, non-volatile optical disk such as a CDROM, DVD-ROM or other optical media can be provided. In such instances, each can be connected to system bus 1212 by one or more data media interfaces. As will be further depicted and described below, storage 1210 may include at least one program product having a set (for example, at least one) of program modules that are configured to carry out the functions of embodiments of the invention. In some embodiments, RAM 1204 is found within storage 1210.

Programs/utilities, having a set (at least one) of program modules, such as the foodborne pathogen detection system 104, may be stored in storage 1210 by way of example, and not limitation, as well as an operating system, one or more application programs, other program modules, and program data. Each of the operating system, one or more application programs, other program modules, and program data or some combination thereof, may include an implementation of a networking environment. Program modules generally carry out the functions and/or methodologies of embodiments of the invention as described herein.

It should be understood that although not shown, other hardware and/or software components could be used in conjunction with the digital device 1200. Examples include, but are not limited to microcode, device drivers, redundant processing units, and external disk drive arrays, RAID systems, tape drives, and data archival storage systems, etc.

Exemplary embodiments are described herein in detail with reference to the accompanying drawings. However, the present disclosure can be implemented in various manners, and thus should not be construed to be limited to the embodiments disclosed herein. On the contrary, those embodiments are provided for the thorough and complete understanding of the present disclosure, and completely conveying the scope of the present disclosure to those skilled in the art.

As will be appreciated by one skilled in the art, aspects of one or more embodiments may be embodied as a system, method or computer program product. Accordingly, aspects may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), a solid state drive (SSD), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program or data for use by or in connection with an instruction execution system, apparatus, or device.

A transitory computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++, Python, or the like and conventional procedural programming languages, such as the "C" programming language or similar programming languages. The computer program code may execute entirely on the light intensity measuring apparatus 102, partly on the light intensity measuring apparatus 102, partly on the light intensity measuring apparatus 102 and partly on the foodborne pathogen detection system 104 or entirely on the foodborne pathogen detection system 104. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

While specific examples are described above for illustrative purposes, various equivalent modifications are possible, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented concurrently or in parallel or may be performed at different times. Further any specific numbers noted herein are only examples: alternative implementations may employ differing values or ranges.

Throughout this specification, plural instances may implement components, operations, or structures described as a single instance. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. Furthermore, any specific numbers noted herein are only examples: alternative implementations may employ differing values or ranges.

Components may be described or illustrated as contained within or connected with other components. Such descriptions or illustrations are examples only, and other configurations may achieve the same or similar functionality. Components may be described or illustrated as "coupled", "couplable", "operably coupled", "communicably coupled" and the like to other components. Such description or illustration should be understood as indicating that such components may cooperate or interact with each other, and may be in direct or indirect physical, electrical, or communicative contact with each other.

Components may be described or illustrated as "configured to", "adapted to", "operative to", "configurable to", "adaptable to", "operable to" and the like. Such description or illustration should be understood to encompass components both in an active state and in an inactive or standby state unless required otherwise by context.

It may be apparent to those skilled in the art that various modifications may be made and other embodiments may be used without departing from the broader scope of the discussion herein. Therefore, these and other variations upon the example embodiments are intended to be covered by the disclosure herein.

The invention claimed is:

1. A system comprising:
   a light intensity measuring apparatus couplable to a food processing apparatus, the light intensity measuring apparatus including:
      a chamber configured to receive a water sample from the food processing apparatus;
      a light source configured to generate light;
      a detector configured to detect the light that has passed through at least a portion of the water sample in the chamber and measure multiple times intensities of wavelengths of the light to obtain multiple sets of measured intensities of wavelengths; and
      a communication module configured to provide the multiple sets of measured intensities of wavelengths; and
   a computing system including:
      at least one processor; and
      memory containing instructions, the instructions being executable by the at least one processor to:
         receive the multiple sets of measured intensities of wavelengths;
         process the multiple sets of measured intensities of wavelengths to obtain a set of values;

apply a first set of decision trees to the set of values to obtain a first result, the first result indicating either a first positive foodborne pathogen detection or a first negative foodborne pathogen detection for a first foodborne pathogen;

generate a first foodborne pathogen detection notification indicating either the first positive foodborne pathogen detection or the first negative foodborne pathogen detection for the first foodborne pathogen; and provide the first foodborne pathogen detection notification.

2. The system of claim 1, the instructions being further executable by the at least one processor to:

apply a second set of decision trees to the set of values to obtain a second result, the second result indicating either a second positive foodborne pathogen detection or a second negative foodborne pathogen detection for a second foodborne pathogen, the second foodborne pathogen different from the first foodborne pathogen;

generate a second foodborne pathogen detection notification indicating either the second positive foodborne pathogen detection or the second negative foodborne pathogen detection for the second foodborne pathogen; and provide the second foodborne pathogen detection notification.

3. The system of claim 1 wherein the instructions being executable by the at least one processor to process the multiple sets of measured intensities of wavelengths to obtain the set of values include instructions being executable by the at least one processor to:

for multiple wavelengths, calculate a particular profile intensity utilizing particular intensities of wavelengths included in the multiple sets of measured intensities of wavelengths to obtain multiple profile intensities;

calculate slopes of the multiple profile intensities at multiple wavelengths to obtain a set of slopes; and apply a fitting function to the set of slopes to obtain the set of values.

4. The system of claim 3, the instructions being further executable by the at least one processor to remove from each of the multiple sets of measured intensities of wavelengths a first set of intensities of wavelengths not associated with presences of one or more pathogens.

5. The system of claim 1 wherein the light intensity measuring apparatus further includes:

a supply valve coupled to a first opening of the chamber and couplable to a water sample supply line couplable to the food processing apparatus;

a drain valve coupled to a second opening of the chamber; and a valve control module configured to control the supply valve to open to allow the water sample from the food processing apparatus to flow into the chamber via the first opening and to control the drain valve to open to allow the water sample to flow out of the chamber via the second opening.

6. The system of claim 5, further comprising:

a cleaning fluid container configured to contain cleaning fluid; and a cleaning fluid supply line couplable to the cleaning fluid container and the supply valve;

wherein the valve control module is further configured to control the supply valve to open to allow cleaning fluid from the cleaning fluid container to flow into the chamber via the first opening and to control the drain valve to open to allow the cleaning fluid to flow out of the chamber via the second opening.

7. The system of claim 6 wherein the light intensity measuring apparatus further includes:

a transducer coupled to the chamber; and a transducer control module configured to control the transducer to move the chamber.

8. A method comprising:

receiving in a chamber of a light intensity measuring apparatus a sample of a food processing byproduct;

generating light to pass through at least a portion of the sample;

detecting the light that has passed through the at least portion of the sample;

measuring multiple times intensities of wavelengths of the light to obtain multiple sets of measured intensities of wavelengths;

processing the multiple sets of measured intensities of wavelengths to obtain a set of values;

applying a first set of decision trees to the set of values to obtain a first result, the first result indicating either a first positive foodborne pathogen detection or a first negative foodborne pathogen detection for a first foodborne pathogen;

generating a first foodborne pathogen detection notification indicating either the first positive foodborne pathogen detection or the first negative foodborne pathogen detection for the first foodborne pathogen; and providing the first foodborne pathogen detection notification.

9. The method of claim 8 further comprising:

applying a second set of decision trees to the set of values to obtain a second result, the second result indicating either a second positive foodborne pathogen detection or a second negative foodborne pathogen detection for a second foodborne pathogen;

generating a second foodborne pathogen detection notification indicating either the second positive foodborne pathogen detection or the second negative foodborne pathogen detection for a second foodborne pathogen; and providing the second foodborne pathogen detection notification.

10. The method of claim 8 wherein processing the multiple sets of measured intensities of wavelengths to obtain the set of values includes:

for multiple wavelengths, calculating a particular profile intensity utilizing particular intensities of wavelengths included in the multiple sets of measured intensities of wavelengths to obtain multiple profile intensities;

calculating slopes of the multiple profile intensities at multiple wavelengths to obtain a set of slopes; and applying a fitting function to the set of slopes to obtain the set of values.

11. The method of claim 10 wherein calculating the particular profile intensity utilizing particular intensities of wavelengths included in the multiple sets of measured intensities of wavelengths to obtain multiple profile intensities includes calculating a particular average intensity utilizing the particular intensities of wavelengths included in the multiple sets of measured intensities of wavelengths to obtain multiple average intensities.

12. The method of claim 10 wherein applying the fitting function to the set of slopes to obtain the set of values includes applying a smoothing filter to the set of slopes to obtain the set of values.

13. The method of claim 10 wherein processing the multiple sets of measured intensities of wavelengths to obtain the set of values further includes removing from each of the multiple sets of measured intensities of wavelengths a first set of intensities of wavelengths not associated with presences of one or more pathogens.

14. The method of claim 8 wherein the light intensity measuring apparatus performs the receiving, the generating light, the detecting, and the measuring, and a foodborne pathogen detection system distinct from the light intensity measuring apparatus performs the processing, the applying, the generating the first foodborne pathogen detection notification and the providing.

15. A non-transitory computer-readable medium comprising executable instructions, the executable instructions being executable by one or more processors to perform a method, the method comprising:
receiving in a chamber of a light intensity measuring apparatus a sample of a food processing byproduct;
generating light to pass through at least a portion of the sample;
detecting the light that has passed through the at least portion of the sample;
measuring multiple times intensities of wavelengths of the light to obtain multiple sets of measured intensities of wavelengths;
processing the multiple sets of measured intensities of wavelengths to obtain a set of values;
applying a first set of decision trees to the set of values to obtain a first result, the first result indicating either a first positive foodborne pathogen detection or a first negative foodborne pathogen detection for a first foodborne pathogen;
generating a first foodborne pathogen detection notification indicating either the first positive foodborne pathogen detection or the first negative foodborne pathogen detection for a first foodborne pathogen; and
providing the first foodborne pathogen detection notification.

16. The non-transitory computer-readable medium of claim 15, the method further comprising:
applying a second set of decision trees to the set of values to obtain a second result, the second result indicating either a second positive foodborne pathogen detection or a second negative foodborne pathogen detection for a second foodborne pathogen;
generating a second foodborne pathogen detection notification indicating either the second positive foodborne pathogen detection or the second negative foodborne pathogen detection for a second foodborne pathogen; and
providing the second foodborne pathogen detection notification.

17. The non-transitory computer-readable medium of claim 15 wherein processing the multiple sets of measured intensities of wavelengths to obtain the set of values includes:
for multiple wavelengths, calculating a particular profile intensity utilizing particular intensities of wavelengths included in the multiple sets of measured intensities of wavelengths to obtain multiple profile intensities;
calculating slopes of the multiple profile intensities at multiple wavelengths to obtain a set of slopes; and
applying a fitting function to the set of slopes to obtain the set of values.

18. The non-transitory computer-readable medium of claim 17 wherein calculating the particular profile intensity utilizing particular intensities of wavelengths included in the multiple sets of measured intensities of wavelengths to obtain multiple profile intensities includes calculating a particular average intensity utilizing the particular intensities of wavelengths included in the multiple sets of measured intensities of wavelengths to obtain multiple average intensities.

19. The non-transitory computer-readable medium of claim 17 wherein applying the fitting function to the set of slopes to obtain the set of values includes applying a smoothing filter to the set of slopes to obtain the set of values.

20. The non-transitory computer-readable medium of claim 15 wherein processing the multiple sets of measured intensities of wavelengths to obtain the set of values further includes removing from each of the multiple sets of measured intensities of wavelengths a set of intensities of wavelengths not associated with presences of one or more pathogens.

* * * * *